US011445807B2

(12) United States Patent
Briggs et al.

(10) Patent No.: US 11,445,807 B2
(45) Date of Patent: Sep. 20, 2022

(54) PUMP CLIP WITH TUBE CLAMP FOR A FLUID INFUSION DEVICE

(71) Applicant: MEDTRONIC MINIMED, INC., Northridge, CA (US)

(72) Inventors: Richard C. Briggs, Santa Clarita, CA (US); Robert C. Castro, Santa Clarita, CA (US); Joseph P. Williams, Northridge, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 179 days.

(21) Appl. No.: 16/945,049

(22) Filed: Jul. 31, 2020

(65) Prior Publication Data

US 2022/0031053 A1 Feb. 3, 2022

(51) Int. Cl.
*A45F 5/02* (2006.01)
*A61M 5/14* (2006.01)

(52) U.S. Cl.
CPC ............ *A45F 5/021* (2013.01); *A61M 5/1414* (2013.01); *A45F 2005/025* (2013.01); *A45F 2200/05* (2013.01)

(58) Field of Classification Search
CPC .. Y10T 24/1391; A45F 5/021; A45F 2200/05; A45F 2005/025; A61M 5/1418; A61M 5/1414

See application file for complete search history.

(56) References Cited

U.S. PATENT DOCUMENTS

| 4,562,751 | A | 1/1986 | Nason et al. |
| 4,678,408 | A | 7/1987 | Nason et al. |
| 4,685,903 | A | 8/1987 | Cable et al. |
| 4,755,173 | A | 7/1988 | Konopka et al. |
| 4,887,753 | A | * 12/1989 | Allen ...................... B60R 11/02 224/558 |
| 5,080,653 | A | 1/1992 | Voss et al. |
| 5,097,122 | A | 3/1992 | Colman et al. |
| 5,391,250 | A | 2/1995 | Cheney, II et al. |
| 5,485,408 | A | 1/1996 | Blomquist |
| 5,505,709 | A | 4/1996 | Funderburk et al. |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,186,982 | B1 | 2/2001 | Gross et al. |
| 6,246,992 | B1 | 6/2001 | Brown |

(Continued)

OTHER PUBLICATIONS

Photograph of a Medtronic Tubing Clamp 7005153-003_B for Paradigm Revel obtained on Jul. 30, 2020, Link: https://www.ebay.com/itm/Authentic-Medtronic-MiniMed-Tubing-Clamps-7005153-003-B-for-Paradigm-Revel/303126481926?hash=item4693bf0c06:g:HogAAOSwuWJavWD8.

*Primary Examiner* — Robert Sandy

(74) *Attorney, Agent, or Firm* — Lorenz & Kopf, LLP

(57) ABSTRACT

A pump clip and a fluid infusion device system, in which the pump clip includes a mount to be connectable to a fluid infusion device, and a base coupled to the mount. The base is pivotable relative to the mount about a first pivot axis. The pump clip includes a clip coupled to the base. The clip is pivotable relative to the base about a second pivot axis, and the clip defines at least one tube clamp to receive a tube associated with the fluid infusion device.

18 Claims, 18 Drawing Sheets

(56) References Cited

U.S. PATENT DOCUMENTS

| | | |
|---|---|---|
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,749,587 B2 | 6/2004 | Flaherty |
| 6,752,299 B2 * | 6/2004 | Shetler ................. F41C 33/045 24/3.11 |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,905,868 B2 | 3/2011 | Moberg et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Mair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 10,449,291 B2 | 10/2019 | Hadian et al. |
| 10,485,924 B2 | 11/2019 | Crane et al. |
| 2003/0106917 A1 * | 6/2003 | Shetler ...................... A45F 5/02 224/269 |
| 2004/0155079 A1 * | 8/2004 | Shetler ................. F41C 33/045 224/269 |
| 2007/0123819 A1 | 5/2007 | Mernoe et al. |
| 2008/0269687 A1 | 10/2008 | Chong et al. |
| 2009/0299290 A1 | 12/2009 | Moberg |
| 2010/0160861 A1 | 6/2010 | Causey, III et al. |

* cited by examiner

PUMP CLIP WITH TUBE CLAMP FOR A FLUID INFUSION DEVICE

TECHNICAL FIELD

The present technology is generally related to fluid infusion devices for delivering a medication fluid to the body of a user. More particularly, embodiments of the subject matter relate to a pump clip for a portable fluid infusion device that securely couples the fluid infusion device to the user and includes a tube clamp to be used with a tube associated with the fluid infusion device.

BACKGROUND

Certain diseases or conditions may be treated, according to modern medical techniques, by delivering a medication or other substance to the body of a user, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens. Other modern systems employ programmable fluid infusion devices (e.g., insulin pumps) to deliver controlled amounts of insulin to a user.

A fluid infusion device suitable for use as an insulin pump may be realized as an external device or an implantable device, which is surgically implanted into the body of the user. Generally, external fluid infusion devices include devices designed for use in a generally stationary location (for example, in a hospital or clinic), and devices configured for ambulatory or portable use (to be carried by a user). External fluid infusion devices may establish a fluid flow path from a fluid reservoir to the user via, for example, a set connector of an infusion set assembly, which is coupled to the fluid reservoir.

In the example of the external fluid infusion device as an insulin infusion device, the external fluid infusion device is intended to be used continuously and delivers insulin twenty-four hours a day according to a programmed plan unique to each pump wearer. A small amount of insulin, or a basal rate, is given continually. This insulin keeps the user's blood glucose levels in the desired range between meals and overnight. When food is eaten, the user programs the external infusion device to deliver a bolus of insulin matched to the amount of food that will be consumed. The user determines how much insulin will be given based on factors including insulin sensitivity, insulin duration, insulin-on-board, and the like. In many instances, external infusion devices include a processor that assists the user in making therapy decisions based on information provided by the user including blood glucose levels, carbohydrate intake, and/or information from the external infusion device.

In this instance, as the device is used continuously for delivering insulin twenty-four hours a day, it is desirable to secure the device to the body of the user. In certain instances, a pump clip can enable easy access to the external infusion device while allowing the fluid infusion device to be securely held in position while being discrete and inconspicuous. In addition, in certain instances, the user may need to perform various tests with the external fluid infusion device, which may require the user to clamp a tube associated with the infusion set assembly.

Accordingly, it is desirable to provide a pump clip for a fluid infusion device that securely couples the fluid infusion device to the user while also providing a tube clamp for clamping a tube associated with the fluid infusion device. Furthermore, other desirable features and characteristics will become apparent from the subsequent detailed description and the appended claims, taken in conjunction with the accompanying drawings and the foregoing technical field and background.

BRIEF SUMMARY

The subject matter of this disclosure generally relates to a pump clip for a fluid infusion device, such as an insulin infusion device, which includes an integrally formed tube clamp to enable the user to easily perform tests of the fluid infusion device.

According to various embodiments, provided is a pump clip for a fluid infusion device system. The pump clip includes a mount to be connectable to a fluid infusion device, and a base coupled to the mount. The base is pivotable relative to the mount about a first pivot axis. The pump clip includes a clip coupled to the base. The clip is pivotable relative to the base about a second pivot axis, and the clip defines at least one tube clamp to receive a tube associated with the fluid infusion device.

Further provided is a fluid infusion device system. The fluid infusion device system includes a fluid infusion device having a pump clip interface, and a pump clip coupled to the pump clip interface. The pump clip includes a mount configured to be slidably received within the pump clip interface. The mount has a first mount end. The pump clip includes a base coupled to the mount at the first mount end. The base is pivotable relative to the mount about a first pivot axis. The base has a first base end. The pump clip includes a clip coupled to the base. The clip is pivotable relative to the base about a second pivot axis. The clip has a first clip end opposite a second clip end, and the clip defines at least one tube clamp proximate the second clip end to receive a tube associated with the fluid infusion device. The first mount end, the first base end and the first clip end extend along an axis, which is transverse to a longitudinal axis of the pump clip to define a support surface for the pump clip.

Also provided is a fluid infusion device system. The fluid infusion device system includes a fluid infusion device having a pump clip interface, and a pump clip coupled to the pump clip interface. The pump clip includes a mount configured to be slidably received within the pump clip interface. The mount has a first mount end. The pump clip includes a base coupled to the mount at the first mount end. The base is pivotable relative to the mount about a first pivot axis, and the base extends for a distance along a longitudinal axis of the pump clip. The base has a first base end. The pump clip includes a clip coupled to the base. The clip is pivotable relative to the base about a second pivot axis. The clip has a first clip end opposite a second clip end, and the clip extends for a second distance along the longitudinal axis, which is greater than the distance of the base. The clip defines at least one tube clamp proximate the second clip end to receive a tube associated with the fluid infusion device. The first mount end, the first base end and the first clip end extend along an axis, which is transverse to a longitudinal axis of the pump clip to define a support surface for the pump clip.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter. The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
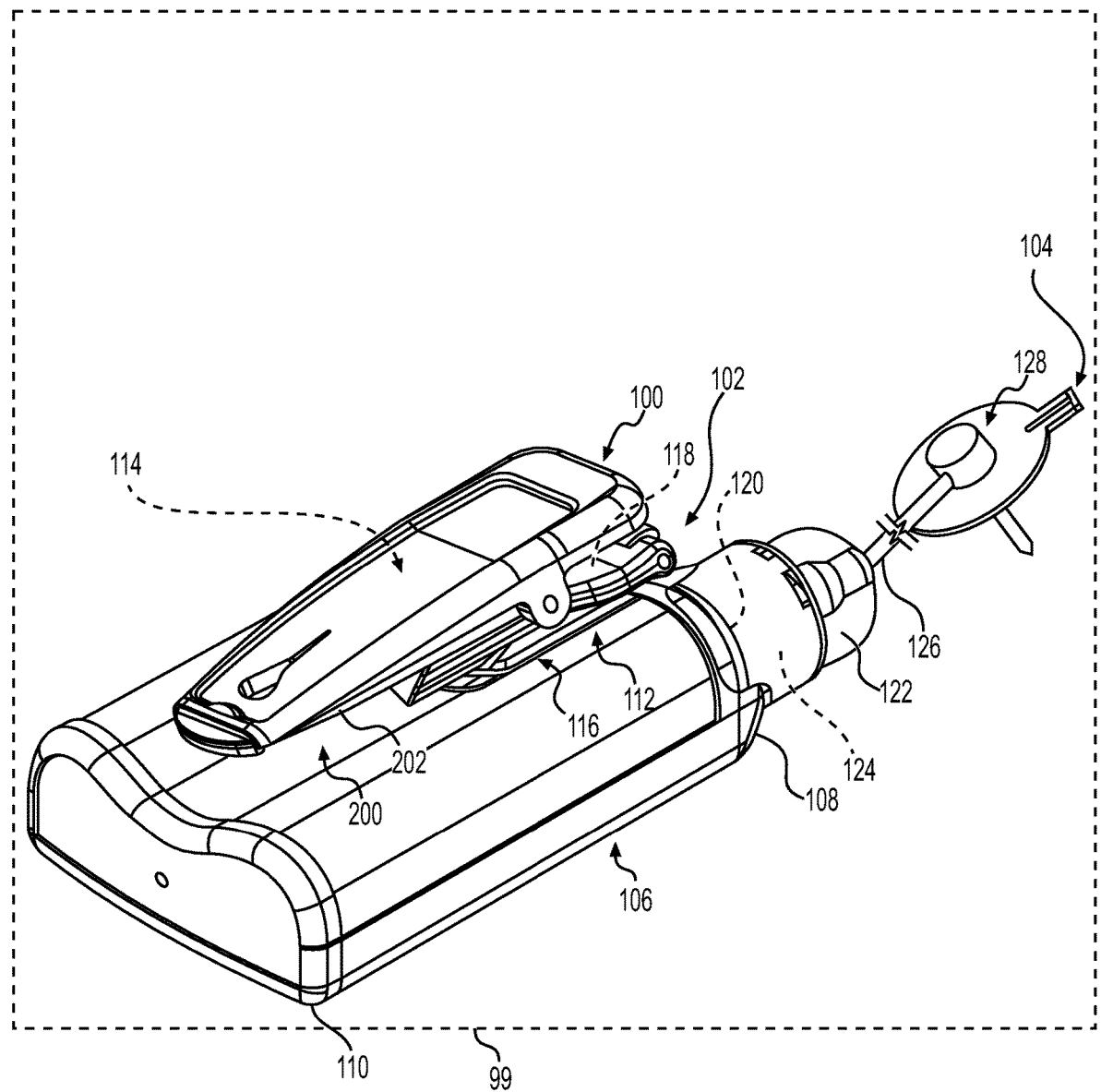
FIG. 1 is a perspective view of an exemplary pump clip with at least one tube clamp for an exemplary fluid infusion device, with the fluid infusion device coupled to an infusion set assembly having a tube, according to various teachings of the present disclosure.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

As used herein, the term "axial" refers to a direction that is generally parallel to or coincident with an axis of rotation, axis of symmetry, or centerline of a component or components. For example, in a cylinder or disc with a centerline and generally circular ends or opposing faces, the "axial" direction may refer to the direction that generally extends in parallel to the centerline between the opposite ends or faces. In certain instances, the term "axial" may be utilized with respect to components that are not cylindrical (or otherwise radially symmetric). For example, the "axial" direction for a rectangular housing containing a rotating shaft may be viewed as a direction that is generally parallel to or coincident with the rotational axis of the shaft. Furthermore, the term "radially" as used herein may refer to a direction or a relationship of components with respect to a line extending outward from a shared centerline, axis, or similar reference, for example in a plane of a cylinder or disc that is perpendicular to the centerline or axis. In certain instances, components may be viewed as "radially" aligned even though one or both of the components may not be cylindrical (or otherwise radially symmetric). Furthermore, the terms "axial" and "radial" (and any derivatives) may encompass directional relationships that are other than precisely aligned with (e.g., oblique to) the true axial and radial dimensions, provided the relationship is predominantly in the respective nominal axial or radial direction. As used herein, the term "transverse" denotes an axis that crosses another axis at an angle such that the axis and the other axis are neither substantially perpendicular nor substantially parallel.

The following description relates to various embodiments of a pump clip. The geometry of the pump clip can be configured to accommodate a variety of different portable devices such as, but not limited to, portable external infusion systems. In one example, the pump clip is provided for use with a fluid infusion device of the type used to treat a medical condition of a user. The infusion device can be used for infusing fluid into the body of a user. The non-limiting examples described below relate to a medical device used to treat diabetes (more specifically, an insulin pump), although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to: U.S. Patent Publication Nos. 2009/0299290 and 2008/0269687; U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; 7,621,893; 7,828,764; and 7,905,868; which are each incorporated by reference herein. Further, for the sake of brevity, conventional aspects and technology related to pump clips may not be described in detail here. In this regard, known and/or conventional aspects of pump clips may be of the type described in, but not limited to: U.S. Pat. Nos. 10,449,291, and 10,485,924 (which are each incorporated by reference herein).

Generally, the pump clip configured to hold an external infusion device, such as a fluid infusion device, has various design challenges that generally are not present regarding many other portable electronic devices. For example, with some embodiments the infusion device is directly connected via tubing to an infusion set having a cannula inserted into the user. Thus, while pump clips for portable electronic devices can allow the electronic device to spin freely, if applied to a portable infusion device the free rotation could lead to tangled or displaced tubing and may displace the infusion set. Moreover, since the pump clip is in contact with the user, the size and geometry of the pump clip needs to be comfortable to wear, and the pump clip needs to be able to attach to a variety of areas on the user or to various articles or objects associated with the user to enable the fluid infusion device to be worn at various locations. Additionally, given the repeated contact with the user, the pump clip needs to be composed of a material resistant to exposure to chemicals, such as sunscreen, body lotion, finger oils, and detergents to prolong a useful life of the pump clip. Moreover, as the pump clip is repeatedly coupled to the user for holding the external fluid infusion device, including a tube clamp on the pump clip ensures that the tube clamp is available to the user in order to perform diagnostic tests on the external infusion device. By including the tube clamp on the pump clip, the user can easily locate the tube clamp to perform the testing as the tube clamp is integrally formed with the pump clip. This improves user satisfaction with the external infusion device, and provides the user with convenience. The pump clip may also be used to open a battery cap associated with the external infusion device to enable the replacement of a battery associated with the external infusion device, which provides the user with added convenience.

Figure 2:
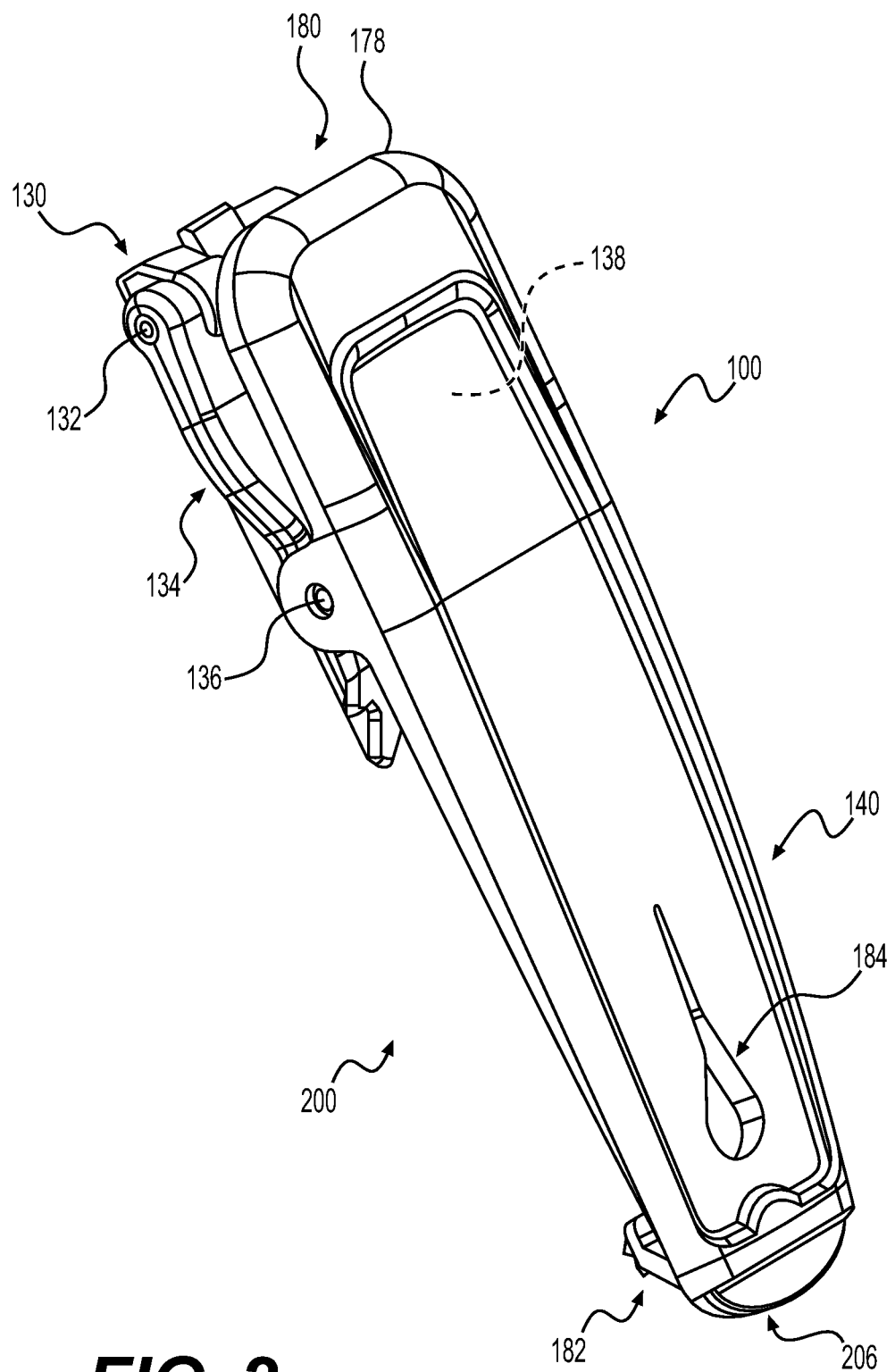
FIG. 2 is perspective view of the pump clip of FIG. 1 removed from the fluid infusion device, in which a clip base is shown in a first position and a clip of the pump clip is shown in a first, clamp position.

With reference to FIG. 1, a pump clip 100 is shown coupled to a fluid infusion device 102, and the fluid infusion device 102 is shown coupled to an infusion set assembly 104. In FIG. 2, the pump clip 100 is shown removed from the fluid infusion device 102. The pump clip 100, the fluid infusion device 102 and the infusion set assembly 104 cooperate to define a portable fluid infusion device system 99 (FIG. 1). The fluid infusion device 102 may be any fluid infusion device known in the art, and thus, the fluid infusion device 102 will not be discussed in great detail herein. Generally, the fluid infusion device 102 is designed to be carried or worn by the user, and to be coupled to the user via the pump clip 100. In one example, the fluid infusion device 102 is an insulin infusion device, such as the MiniMed NGP series Insulin Pump, which is commercially available from Medtronic MiniMed, Inc. of Northridge, Calif. The fluid infusion device 102 may leverage a number of conventional features, components, elements, and characteristics described in U.S. Pat. Nos. 6,485,465, 7,621,893 and 10,485,924, the relevant content of which is incorporated by reference herein.

Figure 1A:
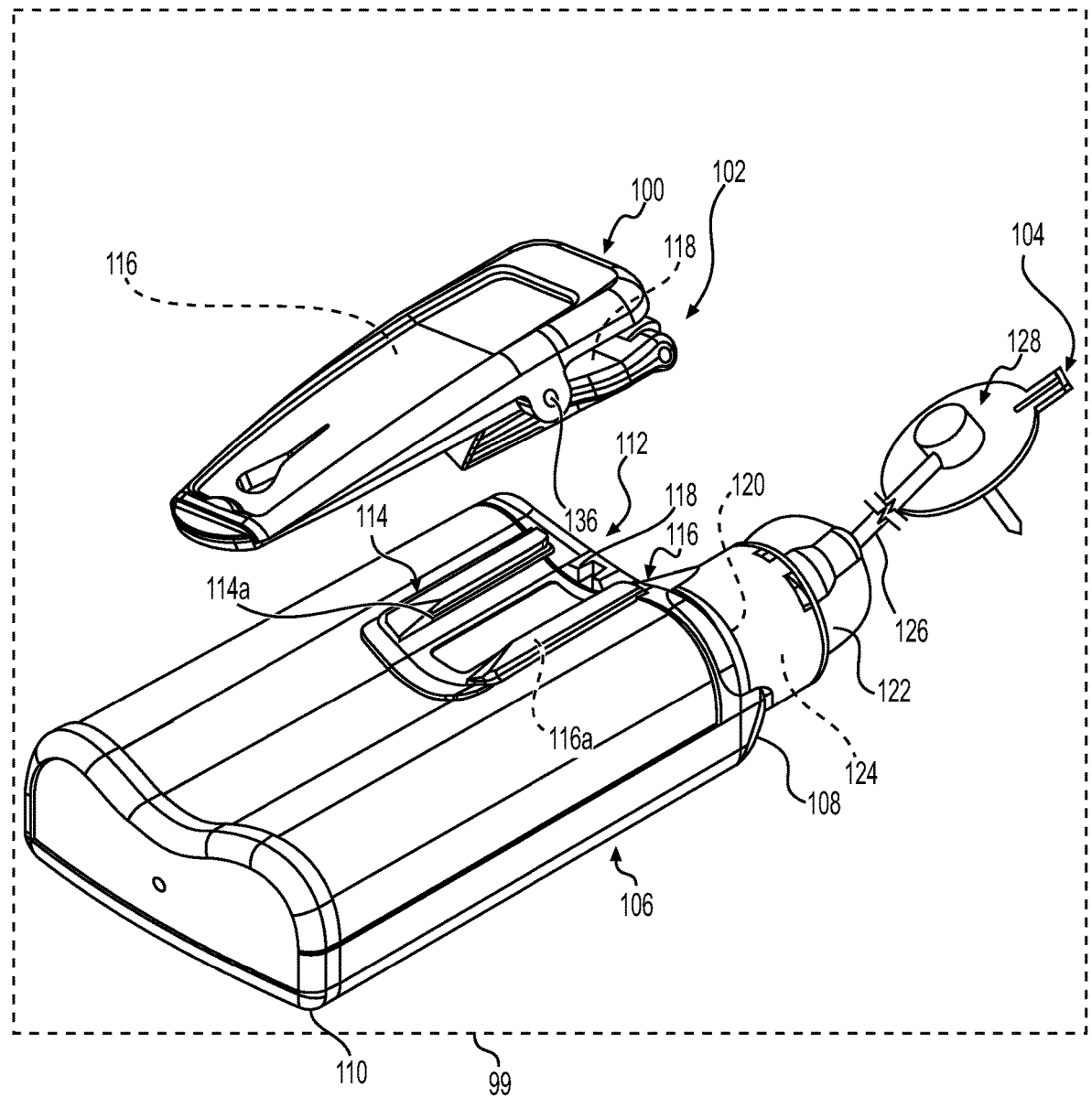
FIG. 1A is a perspective view of the pump clip of FIG. 1 exploded from the fluid infusion device.

Briefly, the fluid infusion device 102 includes a housing 106. The housing 106 has a first end 108 and an opposite second end 110. The first end 108 defines a pump clip plate 112, which with reference to FIG. 1A, includes a first rail 114, a second rail 116 and a knob or notch 118. The first rail 114 and the second rail 116 cooperate to form a pocket that receives a portion of the pump clip 100 to couple the pump clip 100 to the fluid infusion device 102. In one example, the first rail 114 is opposite the second rail 116, and each of the first rail 114 and the second rail 116 define a respective slot 114a, 116a. The slots 114a, 116a slidably receive the portion of the pump clip 100 to couple the pump clip 100 to the fluid infusion device 102. In this example, the slots 114a, 116a extend for a length that is less than a length of the fluid infusion device 102, however, the first rail 114 and the second rail 116 may have any length that is suitable for receiving the portion of the pump clip 100 to couple the pump clip 100 to the housing 106. The notch 118 provides tactile and audible feedback to the user that the pump clip 100 is coupled to the fluid infusion device 102. The notch 118 is substantially U-shaped, and defines a notch recess. The notch recess includes a stop surface that contacts a portion of the pump clip 100 to provide tactile and audible feedback to the user that the pump clip 100 is coupled to the fluid infusion device 102.

The infusion set assembly 104 is coupled to a fluid reservoir 120 associated with the fluid infusion device 102 to define a fluid flow path out of the fluid reservoir 120. In one example, the infusion set assembly 104 includes a connector 122, a hollow instrument or needle 124, a tube 126 and an infusion unit 128. The connector 122 couples the needle 124 and the tube 126 to the fluid reservoir 120, and locks into place once coupled to the fluid reservoir 120 to maintain the fluid flow path between the fluid reservoir 120 and the infusion unit 128. The connector 122 is a removable reservoir cap (or fitting) that is suitably sized and configured to accommodate replacement of the fluid reservoir 120 (which are typically disposable) as needed. The needle 124 defines a flow path for the fluid out of the fluid reservoir 120, through the connector 122 and into the tube 126. From the tube 126, the fluid flows to the infusion unit 128. The infusion unit 128 is coupled to the anatomy of the user, and dispenses the fluid into the anatomy of the user, as is generally known.

With reference to FIG. 2, the pump clip 100 is shown detached from the fluid infusion device 102 (FIG. 1). The pump clip 100 includes a mount 130, a hinge pin 132, a base 134, a clamp pin 136, a spring 138 and a clip 140. The mount 130 couples the pump clip 100 to the fluid infusion device 102. The mount 130 is pivotable along a first pivot axis defined by the hinge pin 132 between a first position and a second position, and various positions in-between to enable a movement of the pump clip 100 relative to the fluid infusion device 102 to absorb forces applied to the fluid infusion device 102 and/or the pump clip 100. The mount 130 is generally composed of biocompatible polymeric material, including, but not limited to, copolyester (Tritan® TX1001 or Tritan® COPOLYESTER MX711), Polyphenylene Sulfide (Fortron® 1200L1), Nylon (Zytel®

Figure 2A:
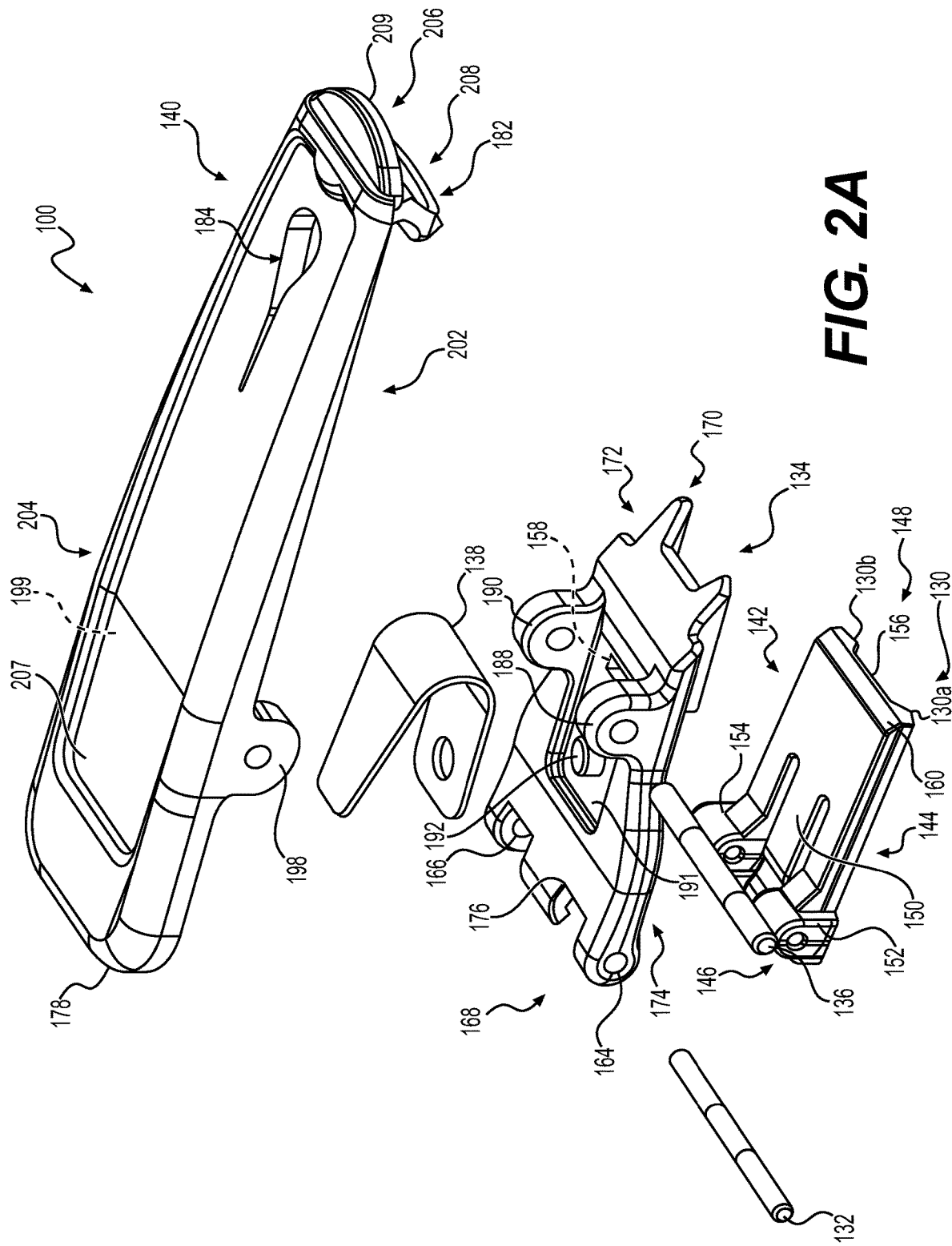
FIG. 2A is an exploded view of the pump clip of FIG. 1.

ST801AW), Polyoxymethylene (Hostaform® MT12U03, Delrin® 500P, and Delrin® SC655), Polyurethane (Isoplast® 2531 or Isoplast® 2510) and polycarbonate. The mount 130 may be formed using casting, printing, molding or another suitable technique. With reference to FIG. 2A, the mount 130 includes a first mount side 142 opposite a second mount side 144, a first mount end 146 opposite a second mount end 148 and a first lock tab 150. The mount 130 is slidably received within the slots 114a, 116a of the rails 114, 116 of the pump clip plate 112 to couple the pump clip 100 to the fluid infusion device 102. In one example, with reference to FIG. 3, opposed arms 130a, 130b of the mount 130 are each slidably received within a respective one of the slots 114a, 116a of the pump clip plate 112 (FIG. 1).

The first mount side 142 includes a first mount pin post 152 and a second mount pin post 154 defined at the first mount end 146. The first mount pin post 152 and the second mount pin post 154 each define a respective mount pin bore, which are coaxially aligned to receive the hinge pin 132. The first mount pin post 152 and the second mount pin post 154 are rounded to provide a smooth surface in case of contact with the user.

Figure 3:
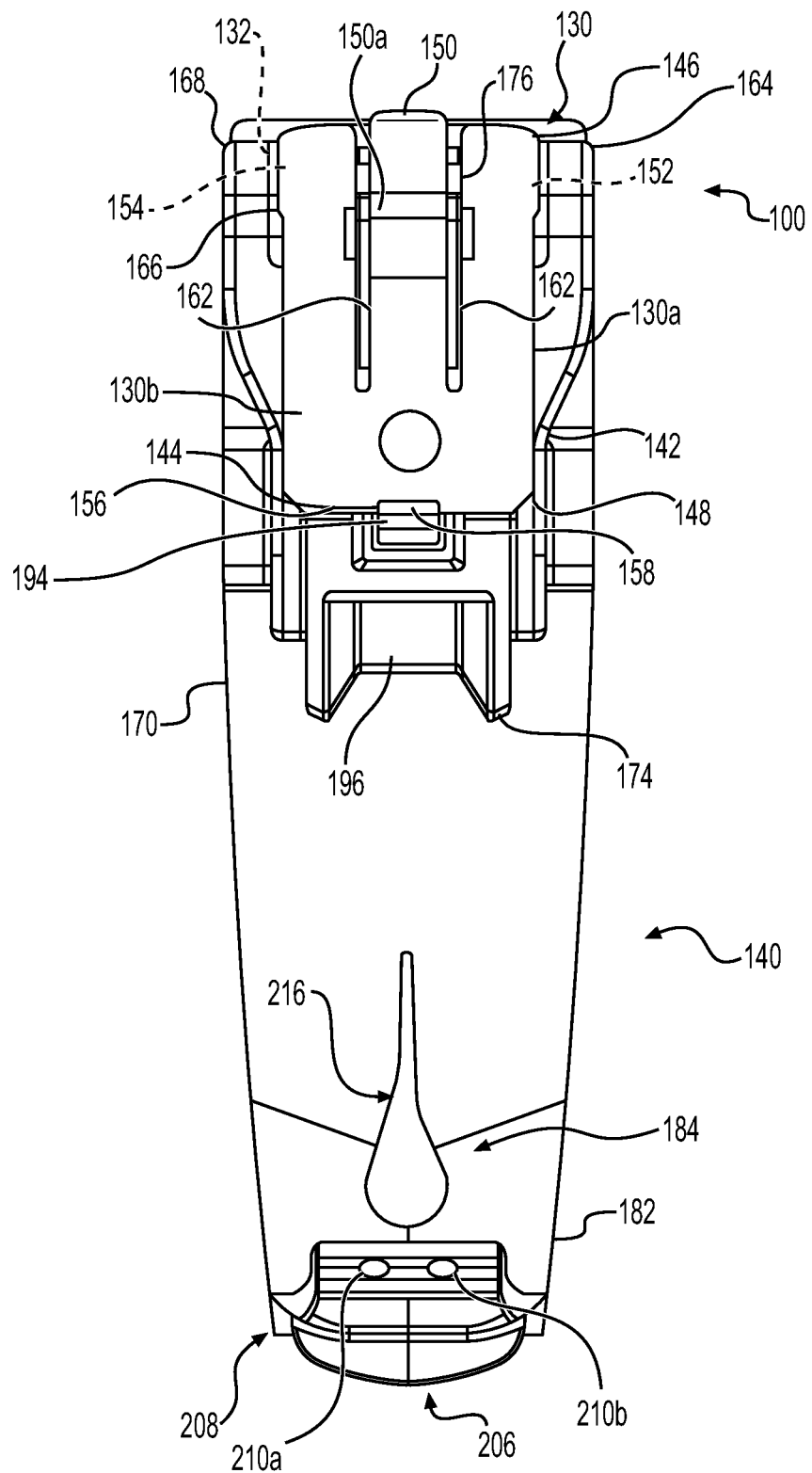
FIG. 3 is a rear view of the pump clip of FIG. 1.
Figure 4:
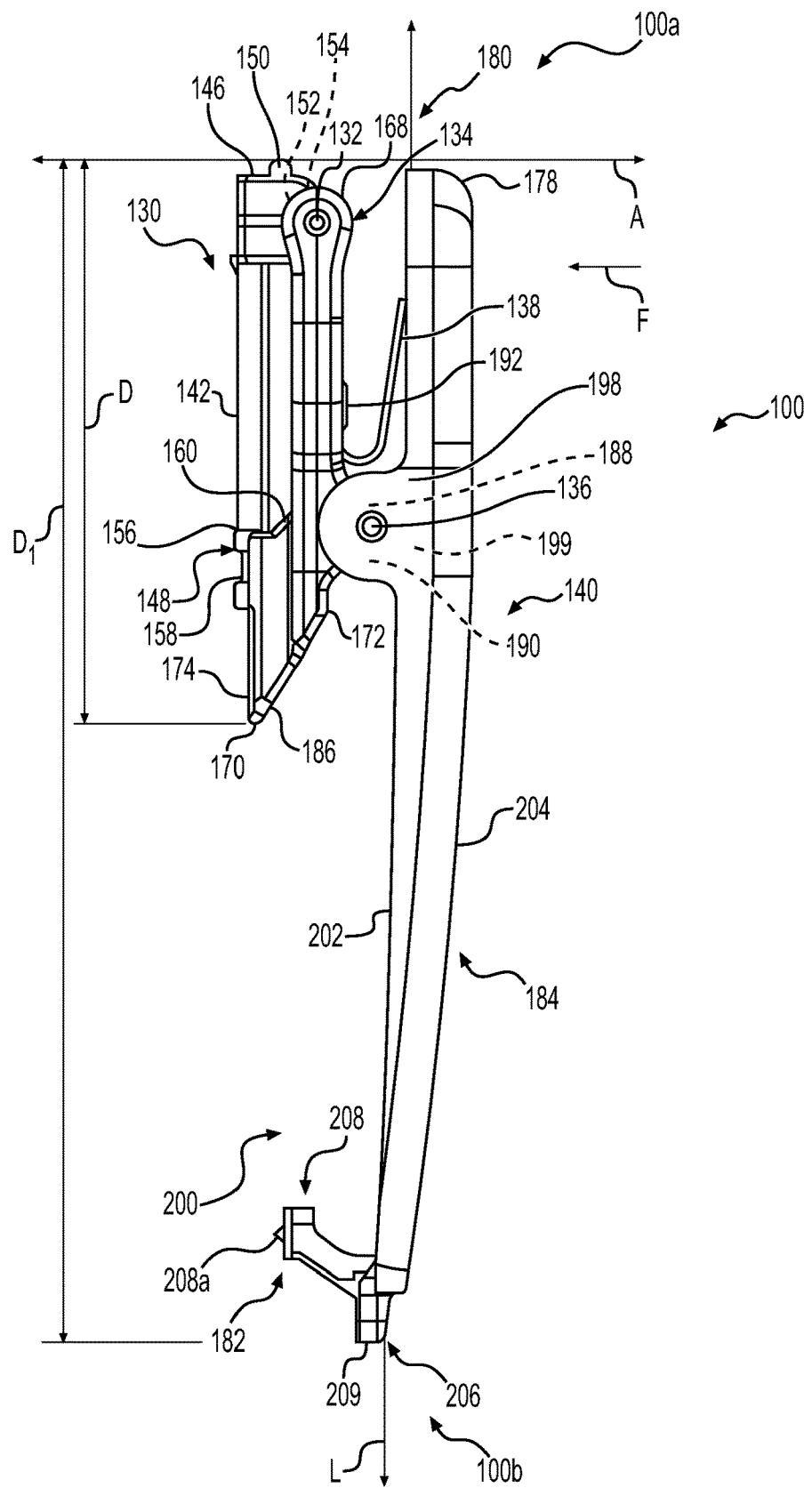
FIG. 4 is side view of the pump clip of FIG. 1.

With reference to FIG. 4, the second mount side 144 defines a lip 156 at the second mount end 148. The lip 156 cooperates with a portion of the base 134 via a snap-fit engagement to maintain the base 134 in a first position as shown in FIG. 4. Upon release of the lip 156 by a force, the mount 130 is pivotable about the first pivot axis defined by the hinge pin 132 to a second position and various positions in-between. In one example, a force acting on the fluid infusion device 102 that is greater than about 3 pound-force (lbf) at the first rail 114 and the second rail 116 of the fluid infusion device 102 causes the release of the lip 156 and the pivoting of the mount 130 about the first pivot axis defined by the hinge pin 132. Thus, the snap-fit engagement between the lip 156 and the portion of the base 134 remains engaged for forces that are less than about 3 pound-force (lbf), and the lip 156 disengages from the portion of the base 134 at forces that are greater than about 3 pound-force (lbf.). In the first position, the mount 130 is adjacent to or next to the base 134, and in the second position, the mount 130 is spaced apart from the base 134. Generally, with reference back to FIG. 3, the lip 156 is defined by a relief at the second mount end 148 that extends inwardly from the second mount side 144 to receive a portion of the base 134. The lip 156 has a width that is configured to withstand a predetermined amount of force before disengaging with the base 134 to enable the mount 130 to move toward the second position and pivot about the first pivot axis defined by the hinge pin 132.

In this regard, a pivotal movement of the base 134 and the clip 140 against the mount 130 about the first pivot axis defined by the hinge pin 132 occurs when the lip 156 disengages from the base 134. The lip 156 disengages when the fluid infusion device 102 and/or pump clip 100 experiences a force via pulling, snagging, bumping, or a force applied by the user to view a screen of the fluid infusion device 102, etc., that is greater than about 3 pound-force (lbf.) while the user is wearing the fluid infusion device 102 with the pump clip 100. Once the lip 156 disengages, the fluid infusion device 102 and the mount 130 rotates about the first pivot axis defined by the hinge pin 132, which dissipates the energy from pulling, snagging, bumping, etc., so that it prevents damage to the pump clip 100 and/or pump clip plate 112 of the fluid infusion device 102. The spring 138 still holds the clip 140 in the first, clamped position onto the base 134, and the fluid infusion device 102 may remain attached to the user's clothing when the lip 156 disengages under the force during pulling, snagging, bumping, etc. Generally, the pump clip 100 can return to the first position prior to the application of the force by applying a force the fluid infusion device 102 to engage the lip 156 to a second lock tab 158 of the base 134.

With reference back to FIG. 4, the second mount end 148 may also define a ramp surface 160 along a width of the second mount end 148. The ramp surface 160 facilitates the engagement of the lip 156 with the portion of the base 134. Generally, a movement of the first lock tab 150 toward the fluid infusion device 102 engages the lip 156 with the base 134, and a movement of the first lock tab 150 away from the fluid infusion device 102 releases the lip 156 from the base 134. Thus, the mount 130 and the base 134 are held together by the engagement of the lip 156 with the base 134.

The first lock tab 150 extends beyond the first mount end 146, and cooperates with the pump clip plate 112 to releasably couple the pump clip 100 to the fluid infusion device 102. In addition, the first lock tab 150 cooperates with the notch 118 to provide tactile and audible feedback to the user that the pump clip 100 is coupled to the fluid infusion device 102. In one example, with reference to FIG. 3, the first lock tab 150 is defined on the mount 130 so as to be cantilevered with regard to the mount 130. In this example, two channels 162 are defined through the first mount side 142 and the second mount side 144 on opposite sides of the first lock tab 150 to enable the first lock tab 150 to move or flex between a first, engaged position and a second, disengaged position to enable the user to couple the pump clip 100 to the fluid infusion device 102 in the first, engaged position and to uncouple the pump clip 100 from the fluid infusion device 102 in the second, disengaged position.

Generally, the first lock tab 150 includes a snap fit feature, which engages with the notch 118 of the fluid infusion device 102 (FIG. 1A) via a snap-fit engagement in the first, engaged position. The snap fit feature, in one example, is a projection 150a, which extends outwardly from the first lock tab 150 on the second mount side 144. The projection 150a provides the tactile and audible feedback to the user when the pump clip 100 is coupled to the fluid infusion device 102. The first lock tab 150 also includes a graspable portion that provides a contact surface for the user to remove or uncouple the pump clip 100 from the fluid infusion device 102.

With reference to FIG. 4, the hinge pin 132 movably or pivotally couples the base 134 to the mount 130, and defines the first pivot axis. The first pivot axis is substantially perpendicular to a longitudinal axis L of the pump clip 100. In one example, the hinge pin 132 may be a stepped pin, having a diameter at a first end and a second end that is less than a diameter of the hinge pin 132 at a midsection. The stepped diameters along the hinge pin 132 reduces stress on the mount 130 and the base 134, and provide a geometrical interference that assists in retaining the hinge pin 132 within the first mount pin post 152, the second mount pin post 154, and within a portion of the base 134. The hinge pin 132 is composed of a biocompatible metal or metal alloy, such as a stainless steel. The hinge pin 132 may be formed through any suitable technique, such as extrusion, stamping, machining, casting, etc. With reference to FIG. 3, the first end of the hinge pin 132 is received within a first pivot arm 164 of the base 134 and through the first mount pin post 152; and the second end of the hinge pin 132 is received within a second pivot arm 166 of the base 134 and through the second mount pin post 154.

The base 134 is generally composed of biocompatible polymeric material, including, but not limited to, copolyester (Tritan® TX1001 or Tritan® COPOLYESTER MX711), Polyphenylene Sulfide (Fortron® 1200L1), Nylon (Zytel® ST801AW), Polyoxymethylene (Hostaform® MT12U03, Delrin® 500P, and Delrin® SC655), Polyurethane (Isoplast® 2531 or Isoplast® 2510) and polycarbonate. The base 134 may be formed using casting, printing, molding or another suitable technique. With reference to FIG. 2A, the base 134 includes a first base end 168 opposite a second base end 170, and a first base side 172 opposite a second base side 174.

The first base end 168 includes the first pivot arm 164, the second pivot arm 166 and the pivot guide 176. The first pivot arm 164, the second pivot arm 166 and the pivot guide 176 are spaced apart along the first base end 168 so that the first mount pin post 152 and the second mount pin post 154 may be received between the first pivot arm 164, the second pivot arm 166 and the pivot guide 176. In one example, the first mount pin post 152 is positioned between the first pivot arm 164 and an end of the pivot guide 176; and the second mount pin post 154 is positioned between an opposite end of the pivot guide 176 and the second pivot arm 166. The first pivot arm 164 defines a first pivot bore, which receives the first end of the hinge pin 132. The second pivot arm 166 defines a second pivot bore, which receives the second end of the hinge pin 132. The pivot guide 176 defines a concave recess, which further guides the base 134 for rotation about the hinge pin 132. In this example, the concave recess contacts the midsection of the hinge pin 132 for guiding the base 134 in rotation about the hinge pin 132. The pivot guide 176 also defines a sloped surface on the second base side 174. The sloped surface provides clearance for the movement or flexing of the first lock tab 150 during coupling and uncoupling of the pump clip 100 from the fluid infusion device 102.

With reference to FIG. 4, the first pivot arm 164, the second pivot arm 166 and the pivot guide 176 also cooperate to serve as a stop for limiting a rotation of the clip 140 relative to the base 134. In addition, the first pivot arm 164, the second pivot arm 166 and the pivot guide 176 cooperate with the mount 130 and a first clip end 178 of the clip 140 to define a substantially planar support surface, generally labeled 180. The support surface 180 is defined along a first end 100a of the pump clip 100. In this example, the first mount end 146 of the mount 130, the first base end 168 of the base 134 and the first clip end 178 of the clip 140 each extend along an axis A, which is transverse to and in this example, perpendicular to the longitudinal axis L of the pump clip 100. As will be discussed, the support surface 180 enables the pump clip 100 to be rested a surface, such as a table or the like, to be free standing or to provide a flat surface to apply a force to facilitate the user's use of a first tube clamp 182 or a second tube clamp 184 (FIG. 3), which are incorporated into the clip 140 proximate a second end 100b of the pump clip 100. The support surface 180 increases a user's leverage when using the first tube clamp 182, and the user is able to use both hands to clamp the tube 126 with the second tube clamp 184. This provides the user with convenience and ease of use, which increases user satisfaction.

The second base end 170 terminates adjacent to the second lock tab 158. Generally, the second base end 170 extends for a distance D along the longitudinal axis L, which is different, and less than a distance D1 that the clip 140 extends. This enables an article of clothing, belt, strap, etc., associated with the user to be received between the clip 140 and the fluid infusion device 102 (FIG. 1). In addition, by extending the distance D, the second base end 170 provides clearance to receive the tube 126 (FIG. 1) through the second tube clamp 184 defined through the clip 140. The second base end 170 also defines an angled surface 186. The angled surface 186 assists in guiding and receiving the article of clothing, belt, strap, etc., associated with the user for coupling the clip 140 to the article of clothing, belt, strap, etc., associated with the user. The angled surface 186 is tapered from the first base side 172 to the second base side 174.

With reference to FIG. 2A, the first base side 172 includes a first clip pin post 188 and a second clip pin post 190. The first base side 172 may also define a recess 191 near the first base end 168 to receive the spring 138. A spring retainer 192 is defined in the recess, and is coupled to the spring 138 to retain the spring 138 on the base 134. In this example, a leaf of the spring 138 engages the recess 191, or pocket, within the base 134. The recess 191, or pocket together with the post or the spring retainer 192, securely holds the leaf of the spring 138.

The first clip pin post 188 and the second clip pin post 190 each extend outwardly and away from the first base side 172. The first clip pin post 188 and the second clip pin post 190 are spaced apart from each other the first base side 172 such that the first clip pin post 188 and the second clip pin post 190 are on opposed sidewalls of the base 134. Generally, the first clip pin post 188 and the second clip pin post 190 are spaced apart to enable the spring 138 to be received between the first clip pin post 188 and the second clip pin post 190. The first clip pin post 188 defines a first clip bore, and the second clip pin post 190 defines a second clip bore. The first clip bore and the second clip bore are coaxially aligned along an axis to receive the clamp pin 136 therethrough to pivotally couple the clip 140 to the base 134. Thus, the hinge pin 132 is used to connect the mount 130 to the base 134 which allows for pivotal movement of the mount 130 relative to the base 134. The hinge pin 132 is inserted through the pair of mount pin bores of the first mount pin post 152 and the second mount pin post 154 of the opposed sidewalls of the mount 130 and the first pivot arm 164 and the second pivot arm 166 of the opposed sidewalls of the base 134.

With reference to FIG. 3, the second base side 174 defines the second lock tab 158, a slot 194 and a recess 196. The second lock tab 158 cooperates with the lip 156. In this regard, in the lock position, the lip 156 is received on or rests on the second lock tab 158. In the unlock position, the lip 156 no longer contacts or is released from the engagement with the second lock tab 158 (FIG. 4). Generally, a thickness of the second lock tab 158 provides an interference onto which the lip 156 is received. The slot 194 enables second lock tab 158 to move or flex to release the lip 156. The slot 194 may be defined between the second lock tab 158 and the first base end 168. The recess 196 may be defined through a portion of the second base side 174 near or adjacent to the second lock tab 158, and may be defined near or adjacent to the second lock tab 158 to the second base end 170. The recess 196 provides a mass savings.

With reference to FIG. 4, the clamp pin 136 movably or pivotally couples the clip 140 to the base 134, and defines a second pivot axis. The second pivot axis is substantially perpendicular to the longitudinal axis L of the pump clip 100, and is substantially parallel to the first pivot axis defined by the hinge pin 132. Generally, the second pivot axis is offset from or spaced apart from the first pivot axis defined by the hinge pin 132 along the longitudinal axis L of the pump clip 100. In one example, with reference to FIG. 2A, the clamp pin 136 may be a stepped pin, having a diameter at a first end and a second end that is less than a diameter of the clamp pin 136 at a midsection. The stepped diameters along the clamp pin 136 reduces stress on the base 134 and the clip 140, and provide a geometrical interference that assists in retaining the clamp pin 136 within the first clip pin post 188, the second clip pin post 190, and within a portion of the clip 140. The clamp pin 136 is composed of a biocompatible metal or metal alloy, such as a stainless steel. The clamp pin 136 may be formed through any suitable technique, such as extrusion, stamping, machining, casting, etc. The first end of the clamp pin 136 is received through the first clip pin post 188; and the second end of the clamp pin 136 is received through the second clip pin post 190. The midsection of the clamp pin 136 is received within a pair of clip coupling posts 198, 199 of the clip 140.

The spring 138 is coupled to the base 134. In one example, the spring 138 is a leaf spring and includes a pair of leaves interconnected by a substantially U-shaped body. The spring 138 is composed of a biocompatible metal or metal alloy, such as a stainless steel. The spring 138 may be extruded, cast, stamped, machined or otherwise formed. The spring 138 is compressible by a force applied to the clip 140 to move the clip 140 from a first, clamped position to a second, release position. In one example, the force needed to overcome the spring 138 to move the clip 140 from the first, clamped position (fully closed position) is about 1 pound-force (lbf.), and the force needed to move the clip 140 to the second, release position (fully opened position) is about 6 pound-force (lbf.). The spring 138 defines a spring bore in one of the leaves for coupling the spring 138 to the spring retainer 192 of the base 134.

The clip 140 defines a slot, generally indicated by reference numeral 200 (FIG. 1), for receipt of an article of clothing or item associated with the user, such as a shirt, belt, strap, etc. between a second clip side 202 of the clip 140 and the fluid infusion device 102 when the clip 140 is in the first, clamped position. The clip 140 is composed of a biocompatible polymeric material, including, but not limited to copolyester (Tritan® TX1001 or Tritan® COPOLYESTER MX711), Polyphenylene Sulfide (Fortron® 1200L1), Nylon (Zytel® ST801AW), Polyoxymethylene (Hostaform® MT12U03, Delrin® 500P, and Delrin® SC655), Polyurethane (Isoplast® 2531 or Isoplast® 2510) and polycarbonate. The clip 140 may be formed using casting, printing, molding or another suitable technique. With reference to FIG. 2A, the clip 140 includes a first clip side 204 opposite the second clip side 202, the first clip end 178 opposite a second clip end 206, the first tube clamp 182 and the second tube clamp 184.

Figure 5:
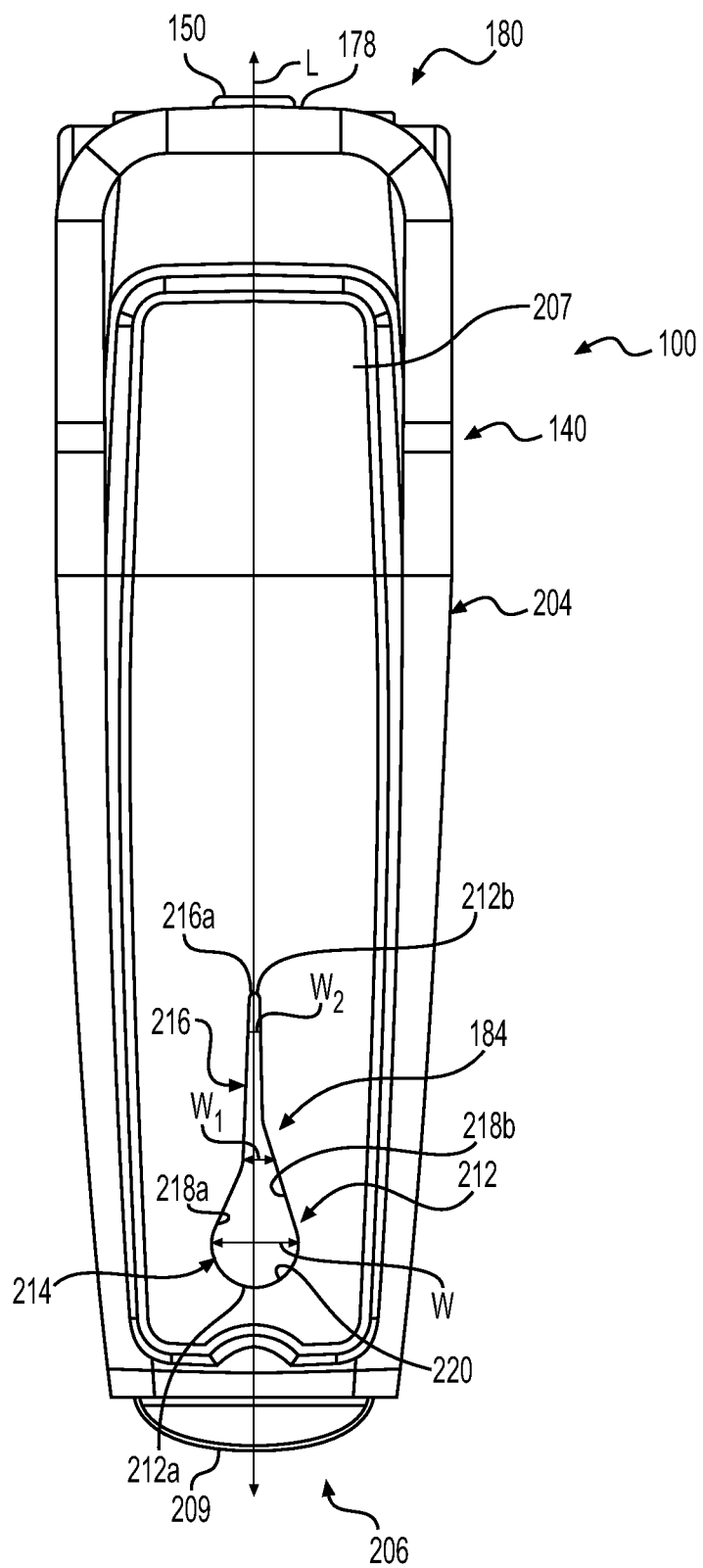
FIG. 5 is a front view of the pump clip of FIG. 1.

With reference to FIG. 5, the first clip side 204 is substantially smooth, and includes a recessed surface 207 that extends from proximate the first clip end 178 to the second clip end 206. The recessed surface 207 provides a location for a removable graphical and/or textual indicator, such as a sticker, decal or decorative skin, which enables the user to personalize the pump clip 100. With reference to FIG. 4, the second clip side 202 is substantially smooth, and includes the pair of clip coupling posts 198, 199, which each extend outwardly from the second clip side 202 near the first clip end 178. The clip coupling posts 198, 199 receive the clamp pin 136. Thus, the clip 140 is rotatably mounted to the base 134 by the clamp pin 136 inserted through the clip coupling posts 198, 199 of the clip 140 and the pair of the clip bores of the first clip pin post 188 and the second clip pin post 190, respectively, on the opposed sidewalls of the base 134.

The second clip side 202 also includes a hook or clip projection 208 at the second clip end 206. With reference to FIG. 4, the clip projection 208 extends outwardly from the second clip side 202, and forms a substantially U-shape with the second clip side 202. The clip projection 208 cooperates with the fluid infusion device 102 (FIG. 1) to define a tortuous path for capturing an article of clothing or other item associated with the user to secure the pump clip 100 to the particular article of clothing or other item. In one example, the clip projection 208 includes a protrusion 208a, which extends outwardly and away from a surface of the clip projection 208. In this example, the protrusion 208a is substantially triangular, and is shaped to engage with the fluid infusion device 102. The engagement of the protrusion 208a assists the pump clip 100 in further clamping or gripping onto an article of clothing or item associated with the user, such as a shirt, belt, strap, etc. Thus, the clip projection 208 enables the clip 140 to clamp onto an article of clothing or other item associated with the user, and the slot 200 also enables the pump clip 100 to be retained about a belt, strap, etc. associated with the user, if desired. Thus, it should be understood that the pump clip 100 is not limited to use just with belts or straps associated with a user. In addition, it should be understood that the clip projection 208 need not include the protrusion 208a, but rather, the clip projection 208 may be rounded, if desired. As will be discussed, in one example, the first tube clamp 182 is defined on the clip projection 208.

The second clip side 202 also has a recess which engages the spring 138. The spring 138 is in compression in the assembly when the clip 140 is in the first, clamped position such that in the first, clamped position shown in FIG. 4, the clip projection 208 at the second clip end 206 of the clip 140 is in compression resting on the fluid infusion device 102 and/or the article associated with the user, which provides better attachment of the pump clip 100 on the article associated with the user, such as a shirt, belt, strap, etc. When a force F applied to the first clip end 178 of the clip 140 exceeds the spring force from the spring 138, the clip 140 rotates about the second pivot axis defined by the clamp pin 136 and the second clip end 206 of the clip 140 is moved to the second, release position in which the clip 140 is open relative to the fluid infusion device 102 (FIG. 1).

Figure 6:
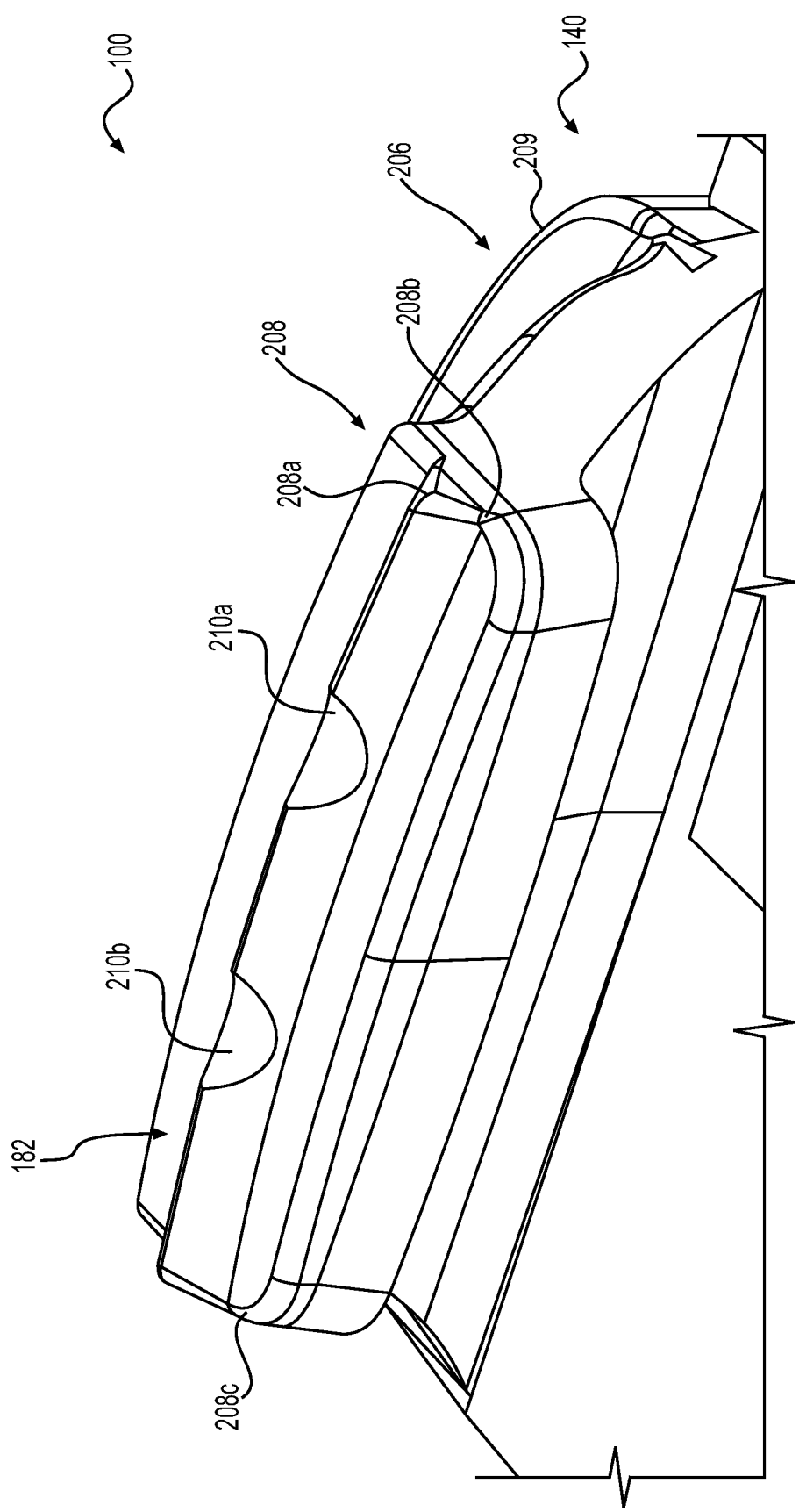
FIG. 6 is a detail perspective view of a first tube clamp associated with the pump clip of FIG. 2.
Figure 6A:
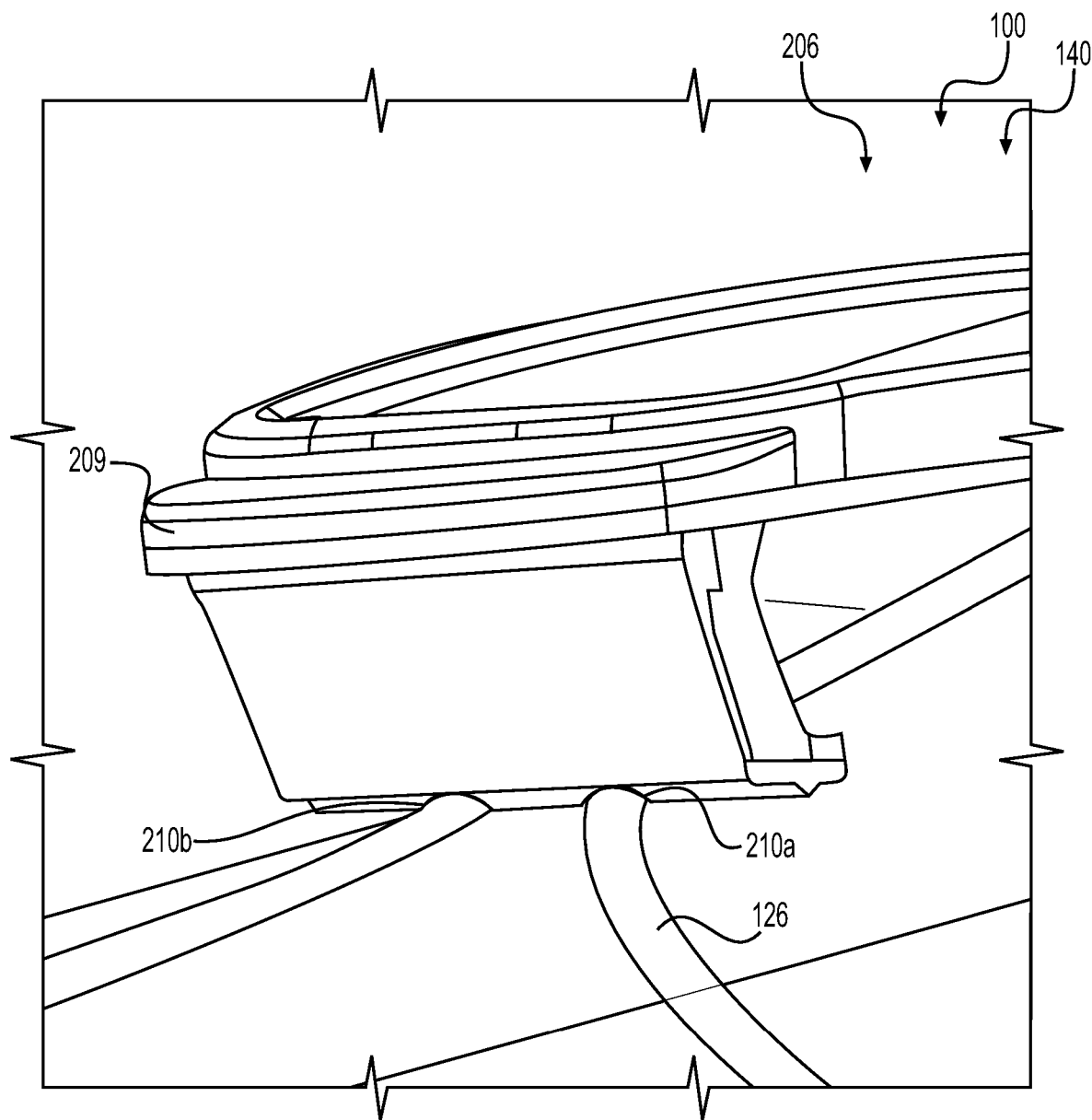
FIG. 6A is a schematic environmental illustration of the pump clip of FIG. 1, in which a first tube clamp is being used to clamp the tube of the infusion set assembly.

In one example, with reference to FIG. 6, the first tube clamp 182 is defined on the protrusion 208a of the clip projection 208. FIG. 6 is a detail view of the first tube clamp 182. In this example, the first tube clamp 182 comprises at least one or a pair of notches 210a, 210b. Each of the notches 210a, 210b is sized and shaped to receive a portion of the tube 126 (FIG. 1) associated with the infusion set assembly 104. Thus, in this example, the notches 210a, 210b define semi-circular recesses, which are spaced apart along the protrusion 208a. In order to clamp the tube 126 (FIG. 1) using the first tube clamp 182, one of the notches 210a, 210b may be aligned and positioned over the tube 126 (FIG. 6A). The user may apply a downward force onto the support surface 180 (FIG. 4), defined by the mount 130, the base 134 and the first clip end 178 (FIG. 4) to compress the tube 126 and inhibit the flow of fluid through the tube 126 when directed during a testing of the fluid infusion device 102 (FIG. 1). It should be noted that the spacing of the notches 210a, 210b in FIG. 6 is merely exemplary, as the notches 210a, 210b may have any desired spacing to clamp the tube 126 (FIG. 1). Generally, however, the notches 210a, 210b are spaced apart from opposed sides 208b, 208c of the clip projection 208 to provide stability during the clamping of the tube 126 (FIG. 1). Moreover, while two notches 210*a*, 210*b* are shown, the protrusion 208*a* may have a single notch 210*a*.

In one example, with reference to FIG. 5, the second tube clamp 184 is defined through the clip 140 from the first clip side 204 to the second clip side 202 proximate the second clip end 206. FIG. 5 is a front view of the pump clip 100. In this example, the second tube clamp 184 comprises a generally tear-drop shaped opening 212, with a bulbous portion or bulbous opening portion 214 in communication with a slit 216. In one example, the opening 212 is asymmetric relative to the longitudinal axis L of the pump clip 100. The bulbous opening portion 214 has a pair of sloped sides 218*a*, 218*b* interconnected by a circular surface 220. The circular surface 220 has a diameter or width W configured to receive the tube 126 (FIG. 1) therethrough, and the pair of sloped sides 218*a*, 218*b* extend upwardly from opposed sides of the circular surface 220 to reduce a size, diameter or circumference of the bulbous opening portion 214. The pair of sloped sides 218*a*, 218*b* define a width W1, which is different and less than the width W. In one example, a sloped side 218*a* has a more gradual slope than a sloped side 218*b* to gradually reduce the size or width of the opening 212. The sloped side 218*b* extends for a distance beyond the sloped side 218*a* to further gradually reduce the size of the opening 212. The slit 216 extends from the pair of sloped sides 218*a*, 218*b* to a terminal point 216*a*. The slit 216 has a width W2, which is different and less than the width W and W1. Thus, the opening 212 transitions from a size or the width W at a first end 212*a* to another size or the width W2 at a second end 212*b*. By transitioning in size, with reference to FIG. 5A, the user may insert a portion of the tube 126 within the bulbous opening portion 214 at the first end 212*a* (FIG. 5A), and gradually push the tube 126 into the slit 216 at the second end 212*b* to inhibit or occlude flow through the tube 126 when directed during a test of the fluid infusion device 102 (FIG. 1). In one example, with continued reference to FIG. 5A, the support surface 180 enables the user to position the pump clip 100 flat on a surface 181, such as a table, resting on the support surface 180, which enables the user to use two hands to insert the portion of the tube 126 into the bulbous opening portion 214 at the first end 212*a* and move the portion of the tube 126 into the slit 216 at the second end 212*b*. By enabling the user to use two hands, a user that may have reduced dexterity can easily use the second tube clamp 184 to inhibit a flow of fluid through the tube 126. Moreover, by providing the support surface 180 for resting the pump clip 100 on a surface, the user is able to use the second tube clamp 184 with ease, which increases user satisfaction.

With reference to FIG. 5, an opener tab 209 extends outwardly at the second clip end 206. The opener tab 209 is generally arcuate or curved, and is shaped to fit within a battery cap (not shown) associated with the fluid infusion device 102. Thus, in certain instances, the user may also employ the pump clip 100 to unlock a battery cap associated with the fluid infusion device 102 to replace a battery, for example. It should be noted that while the opener tab 209 is described herein as being used to open a battery cap associated with the fluid infusion device 102, generally, the opener tab 209 may be used as a flat head screwdriver, and thus, may be used to open or unscrew various other items.

In one example, with reference to FIGS. 2A and 4, in order to assemble the pump clip 100, with each of the mount 130, the hinge pin 132, the base 134, the spring 138, the clamp pin 136 and the clip 140 formed, the base 134 may be coupled to the mount 130 such that the lip 156 of the mount 130 engages the second lock tab 158 of the base 134. With reference to FIG. 3, with the first pivot arm 164 and the second pivot arm 166 of the base 134 coaxially aligned with the first mount pin post 152 and the second mount pin post 154, the hinge pin 132 may be inserted through the first pivot arm 164 and through to the second pivot arm 166 to couple the base 134 to the mount 130. With reference to FIG. 4, the spring 138 may be positioned within the recess defined on the first base side 172, and the spring bore of the spring 138 may be coupled to the spring retainer 192 to couple the spring 138 to the base 134. The clip 140 may be positioned over the base 134 such that the clip coupling posts 198, 199, the first clip pin post 188 and the second clip pin post 190 are coaxially aligned. The clamp pin 136 is inserted through the clip coupling posts 198, 199, the first clip pin post 188 and the second clip pin post 190 to couple the clip 140 to the base 134.

With the pump clip 100 assembled, the pump clip 100 may be coupled to the fluid infusion device 102. In one example, with reference to FIG. 1, with the pump clip plate 112 defined on the fluid infusion device 102, the arms 130*a*, 130*b* on the mount 130 are aligned with the slots 114*a*, 116*a* of the rails 114, 116 on the fluid infusion device 102. The arms 130*a*, 130*b* on the mount 130 are inserted into the rails 114, 116, such that the arms 130*a*, 130*b* slide along the slots 114*a*, 116*a* until the projection 150*a* of the first lock tab 150 engages the notch 118 on the fluid infusion device 102. Once the first lock tab 150 engages, a tactile and audible feedback is provided to the user to indicate the pump clip 100 is fully installed. In FIG. 1, the pump clip 100 is shown fully installed on the fluid infusion device 102.

With the pump clip 100 fully installed on the fluid infusion device 102, the pump clip 100 and the fluid infusion device 102 may be coupled to user. When coupled to the user, the mount 130 is movable relative to the base 134 to compensate for forces applied to the fluid infusion device 102. In one example, with reference to FIG. 4, if the fluid infusion device 402 encounters a force, due to the fluid infusion device 102 encountering a seat belt, arm of a chair, door knob, a force applied by a user, etc., the lip 156 resists the force until the force overcomes the lip 156 and the lip 156 disengages with the base 134. Once the lip 156 disengages from the base 134, the mount 130 moves or pivots from the first position, toward the second position or to a position between the first position and the second position. In the second position, the mount 130 is rotated about the hinge pin 132 away from the base 134, which enables the pump clip 100 to absorb the force, without breaking the pump clip 100 and/or damaging the fluid infusion device 102. By absorbing this force, the pump clip 100 also ensures that the infusion set assembly 104 remains coupled to the user. Alternatively, the user may be the source of the force, as the movement of the mount 130 relative to the base 134 enables the user to rotate the fluid infusion device 102 to view a screen of the fluid infusion device 102 without requiring a removal of the pump clip 100 from the user.

In addition, the clip 140 is movable or pivotable about the second pivot axis defined by the clamp pin 136 based on an application of the force F to the first clip end 178 of the clip 140, which in one example, may range from about 10 degrees to about 45 degrees. It should be understood that the clip 140 may pivot to various other positions between the maximum of about 45 degrees and the first position (FIG. 4), depending upon an amount of the force F applied by the user.

In order to remove or uncouple the pump clip 100 from the fluid infusion device 102, in one example, a force is applied by the user, which lifts up the first lock tab 150. With the first lock tab 150 lifted up, a force is applied by the user to a rear surface of the first lock tab 150 to disengage the lip 156 with the second lock tab 158 of the base 134. Once the lip 156 is disengaged, the pump clip 100 may be moved to slide the arms 130a, 130b toward the notch 118. Once the arms 130a, 130b are removed or disengaged with the slots 114a, 116a of the rails 114, 116, the pump clip 100 is uncoupled or removed from the fluid infusion device 102.

With the pump clip 100 removed from the fluid infusion device 102, the pump clip 100 may be used to perform one or more tests of the fluid infusion device 102. In certain instances, the user may be directed to occlude or inhibit the flow of the fluid through the infusion set assembly 104 (FIG. 1) to diagnose or test certain functions of the fluid infusion device 102. In order to use the first tube clamp 182, when directed, with reference to FIG. 6A, the notches 210a, 210b may be positioned over the tube 126 (FIG. 1). The user may place their hand on the support surface 180 (FIG. 4), and may apply a force to the pump clip 100 to use the notches 210a, 210b to inhibit the flow of the fluid through the tube 126 or to clamp the tube 126 (FIG. 1) with the first tube clamp 182.

Figure 5A:
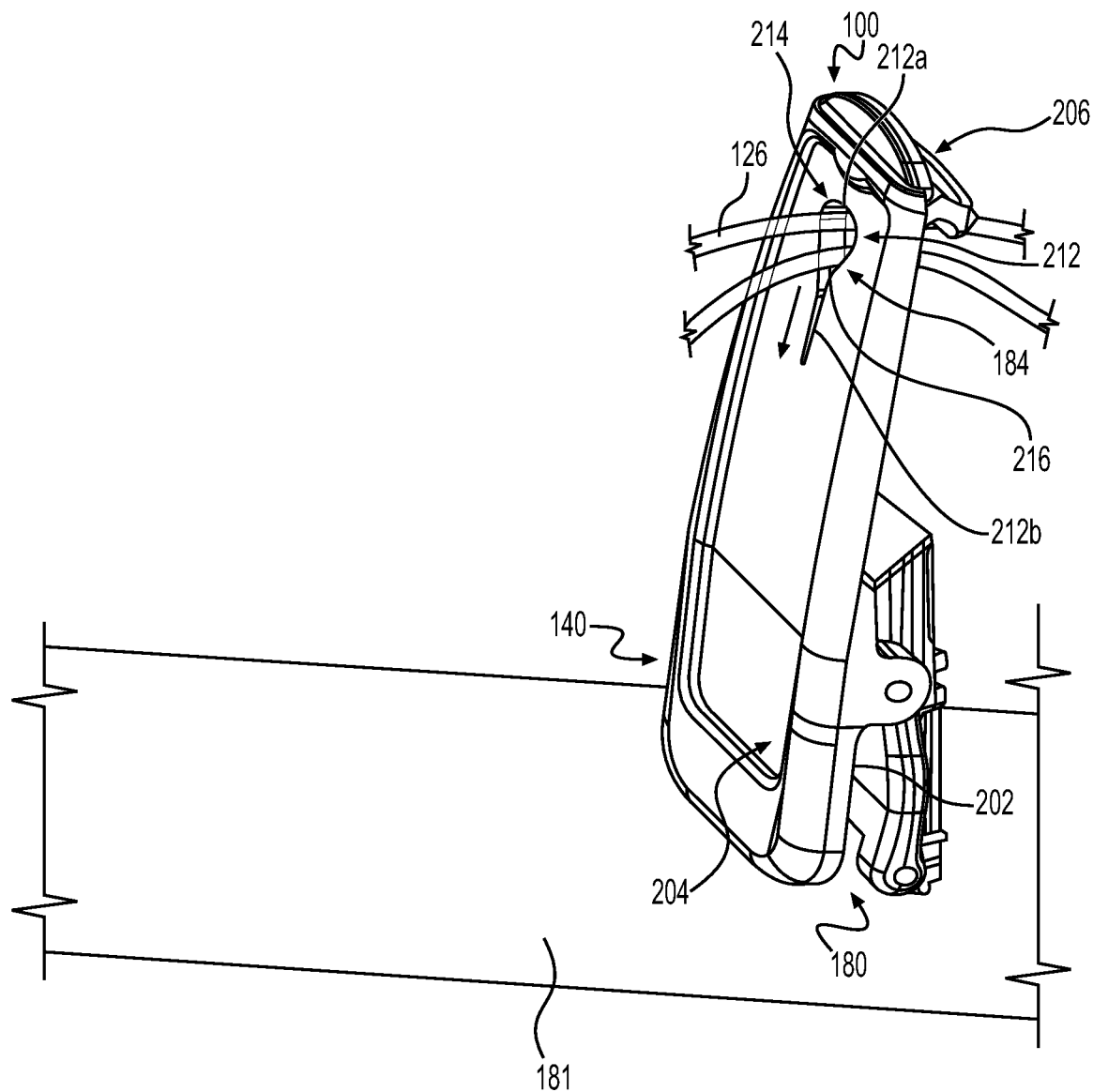
FIG. 5A is a schematic environmental illustration of the pump clip of FIG. 1, in which a second tube clamp is being used to clamp the tube of the infusion set assembly.

Alternatively, with the pump clip 100 removed from the fluid infusion device 102, in order to use the second tube clamp 184 to occlude or inhibit the flow of the fluid through the tube 126 of the infusion set assembly 104 (FIG. 1), when directed, with reference to FIG. 5A, the user may insert the portion of the tube 126 through the bulbous opening portion 214. The user may position the support surface 180 of the pump clip 100 on the surface 181, such as a table, and may push the portion of the tube 126 (FIG. 1) from the bulbous opening portion 214 at the first end 212a toward the slit 216. As the tube 126 (FIG. 1) advances within the opening 212, the portion of the tube 126 is compressed. Once the tube 126 is positioned within the slit 216 at the second end 212b, the flow of the fluid through the tube 126 (FIG. 1) is inhibited such that the tube 126 is clamped by the second tube clamp 184.

Figure 7:
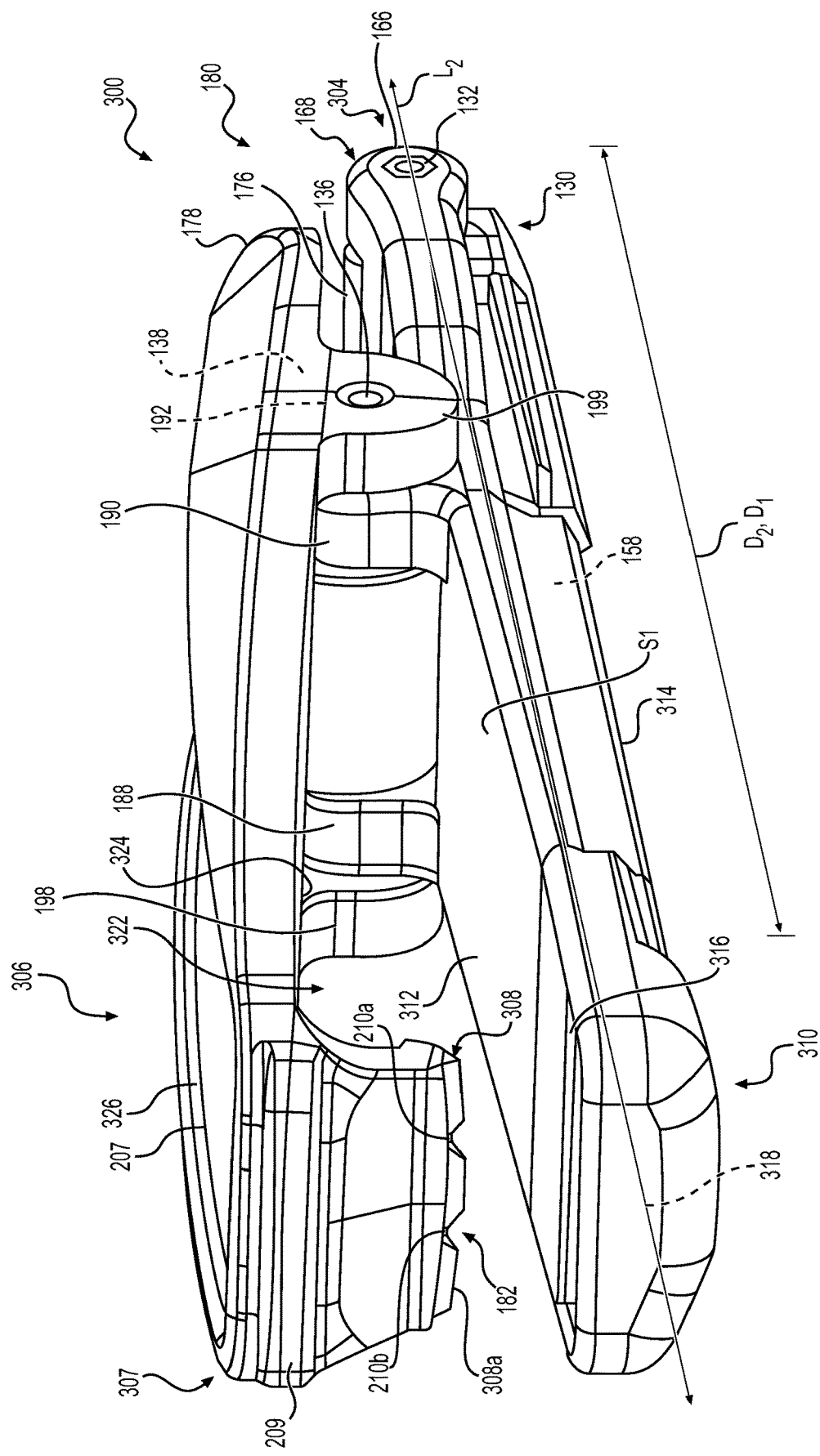
FIG. 7 is a perspective view of another exemplary pump clip with at least one tube clamp, the pump clip for use with the fluid infusion device and the infusion set assembly of FIG. 1, according to various teachings of the present disclosure.

It should be noted that in other embodiments, the pump clip 100 may be configured differently to attach the fluid infusion device 102 to a user while providing a tube clamp. For example, with reference to FIG. 7, a pump clip 300 is shown. As the pump clip 300 includes the same or similar components as the pump clip 100 discussed with regard to FIGS. 1-6, the same reference numerals will be used to denote the same or similar components. FIG. 7 is a perspective view of the pump clip 300 uncoupled from the fluid infusion device 102 (FIG. 1).

The pump clip 300 includes the mount 130, the hinge pin 132, a base 304, the clamp pin 136, the spring 138 and a clip 306. The mount 130 couples the pump clip 300 to the fluid infusion device 102. As discussed, a pivotal movement of the base 304 and the clip 306 against the mount 130 about the first pivot axis defined by the hinge pin 132 occurs when the lip 156 disengages from the base 304. Since the mount 130 is mounted on the fluid infusion device 102 (FIG. 1) and the spring 138 still holds the clip 306 in the first, clamped position onto the base 134, the fluid infusion device 102 remains attached to the user's clothing when the lip 156 disengages under the force during pulling, snagging, bumping, etc.

The base 304 is generally composed of biocompatible polymeric material, including, but not limited to, copolyester (Tritan® TX1001 or Tritan® COPOLYESTER MX711), Polyphenylene Sulfide (Fortron® 1200L1), Nylon (Zytel® ST801AW), Polyoxymethylene (Hostaform® MT12U03, Delrin® 500P, and Delrin® SC655), Polyurethane (Iso-plast® 2531 or Isoplast® 2510) and polycarbonate. The base 304 may be formed using casting, printing, molding or another suitable technique. The base 304 includes the first base end 168 opposite a second base end 310, and a first base side 312 opposite a second base side 314.

The first base end 168 includes the first pivot arm 164, the second pivot arm 166 and the pivot guide 176 as discussed with regard to FIGS. 1-6. In this example, the mount 130, the first base end 168 of the base 134 and the first clip end 178 of the clip 140 each extend along the axis A (not shown), which is transverse to and in this example, perpendicular to the longitudinal axis L2 of the pump clip 300 to define the support surface 180. The support surface 180 provides a flat surface for the application of a force by the user to facilitate the user's use of the first tube clamp 182 incorporated into the clip 306. By being able to apply a force to the support surface 180, a user's leverage is increased, and the user is able to easily use the first tube clamp 182 to clamp the tube 126 (FIG. 1). This provides the user with convenience and ease of use, which increases user satisfaction.

The second base end 310 includes a clip recess 316. The clip recess 316 is defined at or near the second base end 310 and receives a clip projection 308 of the clip 306. The clip recess 316 cooperates with the clip projection 308 of the clip 306 to define a tortuous path for clamping the pump clip 300 to an article of clothing, for example. In this example, the clip recess 316 is substantially rectangular; however, the clip recess 316 may have any desired shape. In this example, the clip recess 316 has an enclosed bottom surface 318, however, it should be understood that the clip recess 316 may comprise an aperture. The bottom surface 318 may also include an indentation, which is configured to mate with the clip projection 308 of the clip 306 to define the tortuous path. In this example, the second base end 310 extends for a distance D2 along the longitudinal axis L2, which is substantially the same as the distance D1 of the clip 306.

The first base side 312 includes the first clip pin post 188 and the second clip pin post 190. The hinge pin 132 is used to connect the mount 130 to the base 304 which allows for pivotal movement of the mount 130 relative to the base 304. The first base side 312 may also define a recess near the first base end 168 to receive the spring 138. The spring retainer 192 is defined in the recess, and is coupled to the spring 138 to retain the spring 138 on the base 304. The first base side 312 also defines a primary surface Si, which is substantially smooth for receiving an article of clothing, belt, strap, etc., associated with the user. The second base side 314 defines the second lock tab 158 and the slot 194. With reference to FIG. 4, the clamp pin 136 movably or pivotally couples the clip 140 to the base 304, and defines the second pivot axis. The spring 138 is coupled to the spring retainer 192 of the base 304.

The clip 306 defines a slot, generally indicated by reference numeral 322, for receipt of an article of clothing or item associated with the user, such as a shirt, belt, strap, etc. between a second clip side 324 of the clip 306 and the first base side 312 of the base 304 when the clip 306 is in the first, clamped position. The clip 306 is composed of a biocompatible polymeric material, including, but not limited to copolyester (Tritan® TX1001 or Tritan® COPOLYESTER MX711), Polyphenylene Sulfide (Fortron® 1200L1), Nylon (Zytel® ST801AW), Polyoxymethylene (Hostaform® MT12U03, Delrin® 500P, and Delrin® SC655), Polyurethane (Isoplast® 2531 or Isoplast® 2510) and polycarbonate. The clip 306 may be formed using casting, printing, molding or another suitable technique. The clip 306 includes a first clip side 326 opposite the second clip side 324, the first clip end 178 opposite a second clip end 307 and the first tube clamp 182.

The first clip side 326 is substantially smooth, and includes the recessed surface 207 that extends from proximate the first clip end 178 to the second clip end 307. The second clip side 324 is substantially smooth, and includes the clip coupling posts 198, 199, which each extend outwardly from the second clip side 324 near the first clip end 178. The clip coupling posts 198, 199 receive the clamp pin 136. The second clip side 324 also includes the hook or clip projection 308 at the second clip end 307. The clip projection 308 extends outwardly from the second clip side 324, and forms a substantially U-shape with the second clip side 324. The clip projection 308 cooperates with the fluid infusion device 102 (FIG. 1) to define a tortuous path for capturing an article of clothing or other item associated with the user to secure the pump clip 300 to the particular article of clothing or other item. In one example, the clip projection 308 includes a protrusion 308a, which extends outwardly and away from a surface of the clip projection 308. In this example, the protrusion 308a is substantially triangular, and is shaped to engage with the fluid infusion device 102. The engagement of the protrusion 308a assists the pump clip 300 in further clamping or gripping onto an article of clothing or item associated with the user, such as a shirt, belt, strap, etc. Thus, the clip projection 308 enables the clip 306 to clamp onto an article of clothing or other item associated with the user. The clip projection 308 cooperates with the clip recess 316 to define a tortuous path for capturing an article of clothing or other item associated with the user to secure the pump clip 300 to the particular article of clothing or other item. In addition, it should be understood that the clip projection 308 need not include the protrusion 308a, but rather, the clip projection 308 may be rounded, if desired. The second clip side 324 also engages with the spring 138.

In this example, the first tube clamp 182 is defined on a protrusion 308a of the clip projection 308. As discussed, the first tube clamp 182 comprises the pair of notches 210a, 210b. Thus, in this example, the pump clip 300 includes the first tube clamp 182 and is devoid of the second tube clamp 184. The pump clip 300 may also include the opener tab 209, which extends outwardly at the second clip end 307. The opener tab 209 is generally arcuate or curved, and is shaped to fit within a battery cap (not shown) associated with the fluid infusion device 102. In certain instances, the user may also employ the pump clip 300 to unlock a battery cap associated with the fluid infusion device 102 to replace a battery, for example. It should be noted that while the opener tab 209 is described herein as being used to open a battery cap associated with the fluid infusion device 102, generally, the opener tab 209 may be used as a flat head screwdriver, and thus, may be used to open or unscrew various other items.

As the assembly of the pump clip 300, the coupling and uncoupling of the pump clip 300 to the fluid infusion device 102 and the use of the first tube clamp 182 is the same as that discussed with regard to FIGS. 1-6, the assembly, the coupling and uncoupling of the pump clip 300 from the fluid infusion device 102 and the use of the first tube clamp 182 associated with the pump clip 300 will not be discussed in detail herein as one skilled in the art would understand how to use the pump clip 300 based on the discussion regarding the pump clip 100.

Figure 7A:
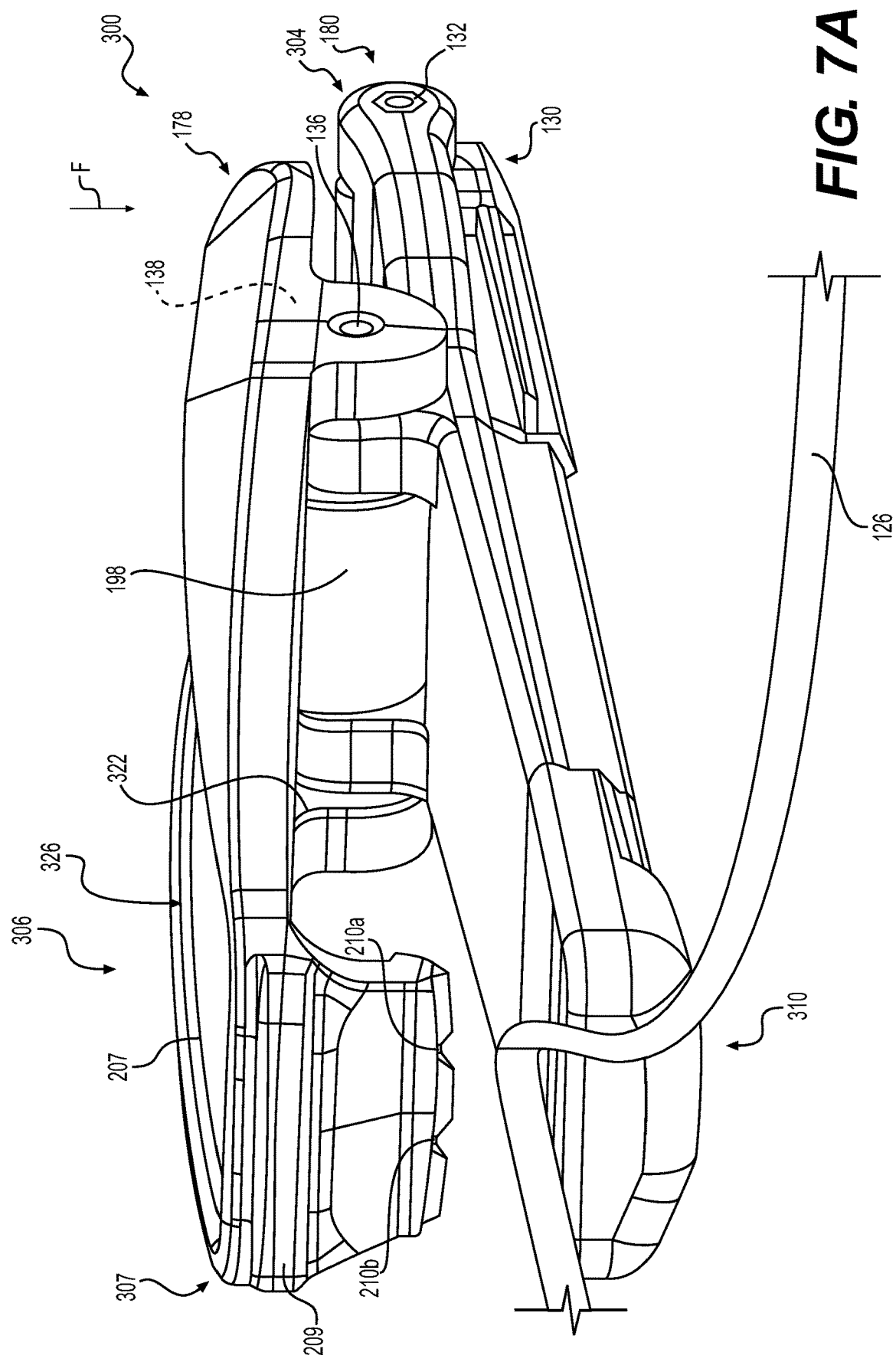
FIG. 7A is a schematic environmental illustration of the pump clip of FIG. 1, in which a first tube clamp is being used to clamp the tube of the infusion set assembly.

Briefly, however, with the pump clip 300 removed from or uncoupled from the fluid infusion device 102, the pump clip 300 may be used to perform one or more tests of the fluid infusion device 102. In certain instances, the user may be directed to occlude or inhibit the flow of the fluid through the infusion set assembly 104 (FIG. 1) to diagnose or test certain functions of the fluid infusion device 102. In order to use the first tube clamp 182, when directed, with reference to FIG. 7A, the user may place their hand on the first clip end 178 to apply the force F to the pump clip 300 to overcome the force of the spring 138 and pivot the clip 306 relative to the base 304 about the clamp pin 136. The notches 210a, 210b may be positioned over the tube 126. The user may remove their hand from the first clip end 178, and the force of the spring 138 pivots the clip 306 toward the base 304, which clamps the tube 126 between the notches 210a, 210b to inhibit the flow of the fluid through the tube 126 or to clamp the tube 126 with the first tube clamp 182.

It should be noted that in other embodiments, the pump clip 100 may be configured differently to attach the fluid infusion device 102 to a user while providing a tube clamp. For example, with reference to FIG. 8, a pump clip 400 is shown. As the pump clip 400 includes the same or similar components as the pump clip 100 discussed with regard to FIGS. 1-6, the same reference numerals will be used to denote the same or similar components.

Figure 8:
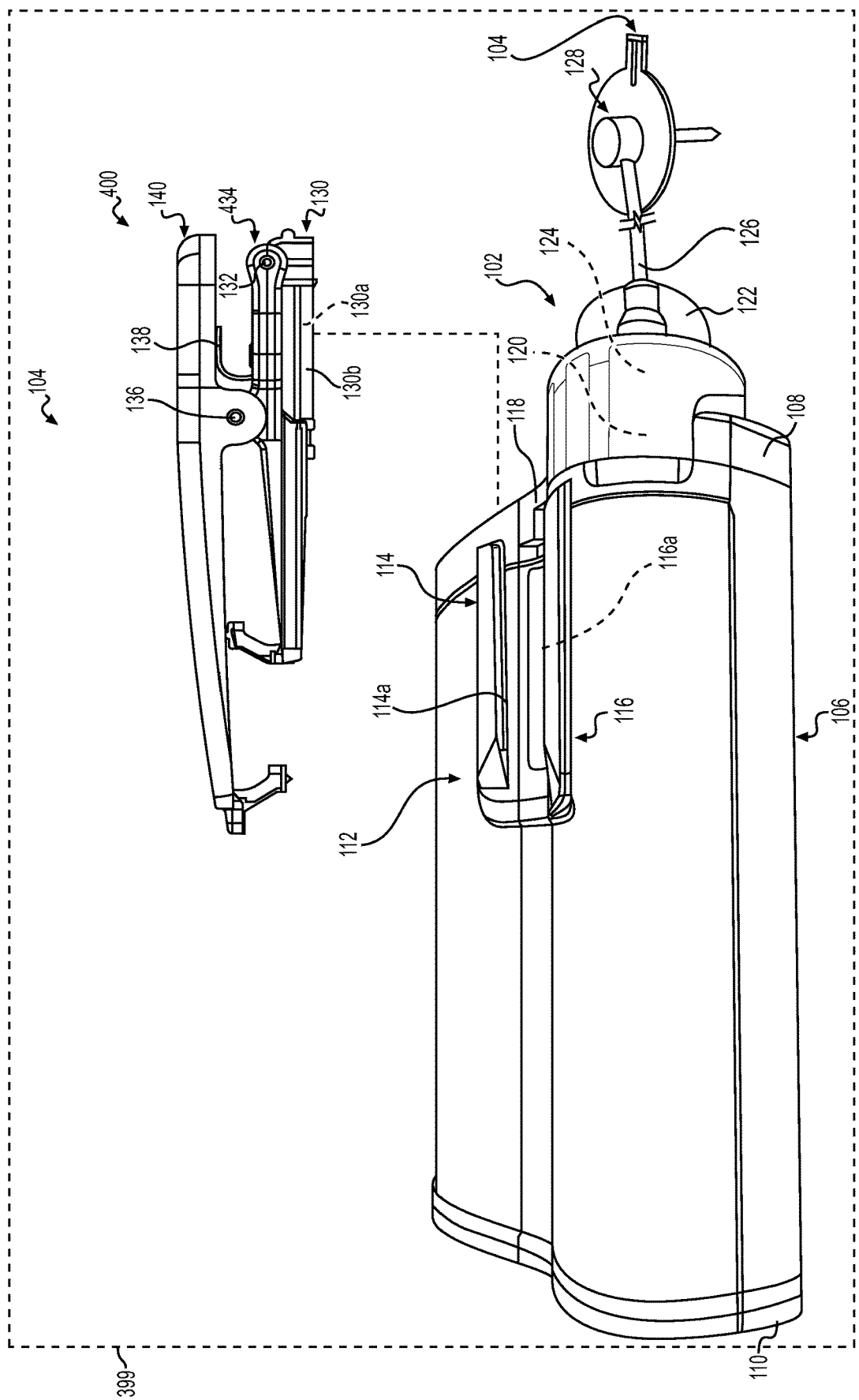
FIG. 8 is a perspective view of another exemplary pump clip with at least one tube clamp exploded from the fluid infusion device and the fluid infusion device is coupled to the infusion set assembly having the tube, according to various teachings of the present disclosure.
Figure 9:
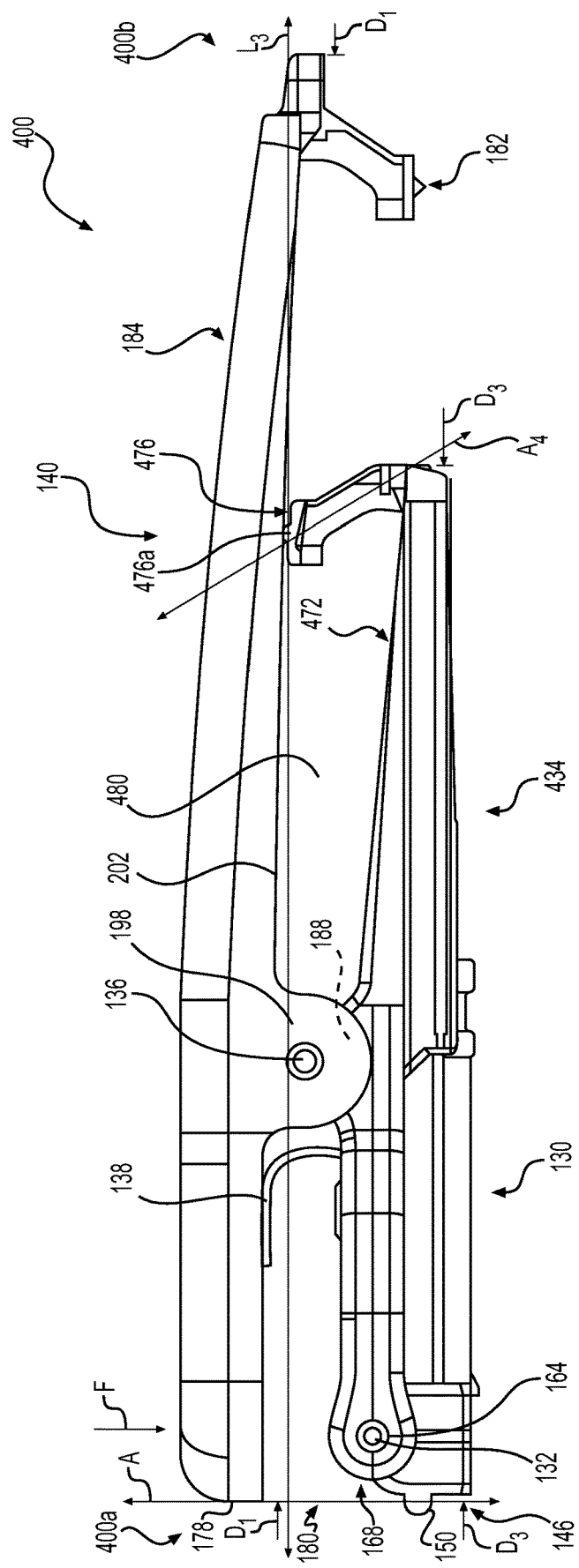
FIG. 9 is a side view of the pump clip of FIG. 8.

With reference to FIG. 8, the pump clip 400 is shown exploded from the fluid infusion device 102, and the fluid infusion device 102 is shown coupled to the infusion set assembly 104. In FIG. 9, the pump clip 400 is shown removed from the fluid infusion device 102. The pump clip 400, the fluid infusion device 102 and the infusion set assembly 104 cooperate to define a portable fluid infusion device system 399 (FIG. 8).

As discussed, the fluid infusion device 102 includes the housing 106. The first end 108 defines the pump clip plate 112 (FIG. 8), which includes the first rail 114, the second rail 116 and the knob or notch 118. The first rail 114 and the second rail 116 cooperate to form a pocket that receives a portion of the pump clip 400 to couple the pump clip 400 to the fluid infusion device 102. In one example, the first rail 114 is opposite the second rail 116, and each of the first rail 114 and the second rail 116 define a respective slot 114a, 116a. The slots 114a, 116a slidably receive the portion of the pump clip 400 to couple the pump clip 400 to the fluid infusion device 102. In this example, the slots 114a, 116a extend for a length that is less than a length of the fluid infusion device 102, however, the first rail 114 and the second rail 116 may have any length that is suitable for receiving the portion of the pump clip 400 to couple the pump clip 400 to the housing 106. The notch 118 provides tactile and audible feedback to the user that the pump clip 400 is coupled to the fluid infusion device 102. The notch 118 is substantially U-shaped, and defines a notch recess. The notch recess includes a stop surface that contacts a portion of the pump clip 400 to provide tactile and audible feedback to the user that the pump clip 400 is coupled to the fluid infusion device 102. As discussed, the infusion set assembly 104 is coupled to the fluid reservoir 120 associated with the fluid infusion device 102 to define a fluid flow path out of the fluid reservoir 120. In one example, the infusion set assembly 104 includes the connector 122, the hollow instrument or needle 124, the tube 126 and the infusion unit 128.

Figure 10:
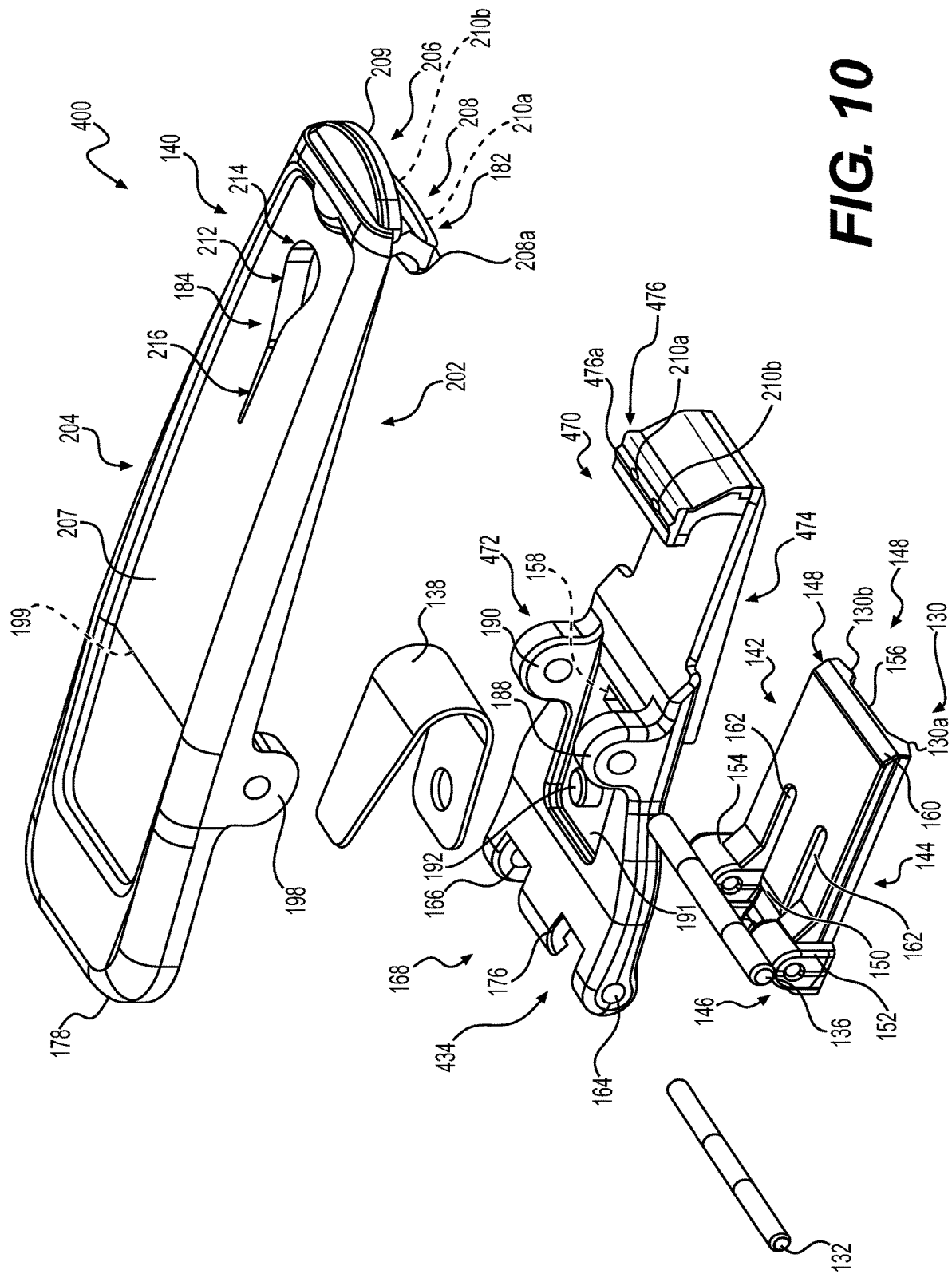
FIG. 10 is an exploded view of the pump clip of FIG. 8.

In FIG. 9, the pump clip 400 is shown detached from the fluid infusion device 102 (FIG. 8). With reference to FIG. 10, the pump clip 400 includes the mount 130, the hinge pin 132, a base 434, the clamp pin 136, the spring 138 and the clip 140. The mount 130 couples the pump clip 400 to the fluid infusion device 102 (FIG. 8). The mount 130 is pivotable along a first pivot axis defined by the hinge pin 132 between a first position and a second position, and various positions in-between to enable a movement of the pump clip 400 relative to the fluid infusion device 102 to absorb forces applied to the fluid infusion device 102 and/or the pump clip 400. The mount 130 is slidably received within the slots 114a, 116a of the rails 114, 116 of the pump clip plate 112 to couple the pump clip 400 to the fluid infusion device 102. In one example, with reference to FIG. 8, opposed arms 130a, 130b of the mount 130 are each slidably received within a respective one of the slots 114a, 116a of the pump clip plate 112.

The first mount side 142 includes the first mount pin post 152 and the second mount pin post 154 defined at the first mount end 146 to receive the hinge pin 132. The second mount side 144 defines the lip 156 at the second mount end 148. The lip 156 cooperates with a portion of the base 434 via a snap-fit engagement to maintain the base 434 in a first position as shown in FIG. 8. Upon release of the lip 156 by a force, the mount 130 is pivotable about the first pivot axis defined by the hinge pin 132 to a second position and various positions in-between. In one example, a force acting on the fluid infusion device 102 that is greater than about 3 pound-force (lbf) at the first rail 114 and the second rail 116 of the fluid infusion device 102 causes the release of the lip 156 and the pivoting of the mount 130 about the first pivot axis defined by the hinge pin 132. Thus, the snap-fit engagement between the lip 156 and the portion of the base 434 remains engaged for forces that are less than about 3 pound-force (lbf.), and the lip 156 disengages from the portion of the base 434 at forces that are greater than about 3 pound-force (lbf). In the first position, the mount 130 is adjacent to or next to the base 434, and in the second position, the mount 130 is spaced apart from the base 434. Generally, the lip 156 is defined by a relief at the second mount end 148 that extends inwardly from the second mount side 144 to receive a portion of the base 434. The lip 156 has a width that is configured to withstand a predetermined amount of force before disengaging with the base 434 to enable the mount 130 to move toward the second position and pivot about the first pivot axis defined by the hinge pin 132.

In this regard, a pivotal movement of the base 434 and the clip 140 against the mount 130 about the first pivot axis defined by the hinge pin 132 occurs when the lip 156 disengages from the base 434. The lip 156 disengages when the fluid infusion device 102 and/or pump clip 400 experiences a force via pulling, snagging, bumping, or a force applied by the user to view a screen of the fluid infusion device 102, etc., that is greater than about 3 pound-force (lbf.) while the user is wearing the fluid infusion device 102 (FIG. 8) with the pump clip 400. Once the lip 156 disengages, the fluid infusion device 402 and the mount 130 rotates about the first pivot axis defined by the hinge pin 132, which dissipates the energy from pulling, snagging, bumping, etc., so that it prevents damage to the pump clip 400 and/or pump clip plate 112 of the fluid infusion device 102. Since the mount 130 is mounted on the fluid infusion device 102 and the spring 138 still holds the clip 140 in the first, clamped position onto the base 434, the fluid infusion device 102 remains attached to the user's clothing due between the contact between the base 434 and the clip 140 when the lip 156 disengages under the force during pulling, snagging, bumping, etc. Generally, the pump clip 400 can return to the first position prior to the application of the force by applying a force the fluid infusion device 102 to engage the lip 156 to a second lock tab 158 of the base 434.

With reference back to FIG. 10, the second mount end 148 may also define the ramp surface 160 along a width of the second mount end 148. The ramp surface 160 facilitates the engagement of the lip 156 with the portion of the base 434. Generally, a movement of the first lock tab 150 toward the fluid infusion device 102 engages the lip 156 with the base 434, and a movement of the first lock tab 150 away from the fluid infusion device 102 releases the lip 156 from the base 434. Thus, the mount 130 and the base 434 are held together by the engagement of the lip 156 with the base 434.

With reference to FIG. 10, the first lock tab 150 extends beyond the first mount end 146, and cooperates with the pump clip plate 112 (FIG. 8) to releasably couple the pump clip 400 to the fluid infusion device 102. In addition, the first lock tab 150 cooperates with the notch 118 (FIG. 8) to provide tactile and audible feedback to the user that the pump clip 400 is coupled to the fluid infusion device 102. In one example, with reference to FIG. 10, the first lock tab 150 is defined on the mount 130 so as to be cantilevered with regard to the mount 130. In this example, the two channels 162 are defined through the first mount side 142 and the second mount side 144 on opposite sides of the first lock tab 150 to enable the first lock tab 150 to move or flex between a first, engaged position and a second, disengaged position to enable the user to couple the pump clip 400 to the fluid infusion device 102 in the first, engaged position and to uncouple the pump clip 400 from the fluid infusion device 102 in the second, disengaged position.

Figure 11:
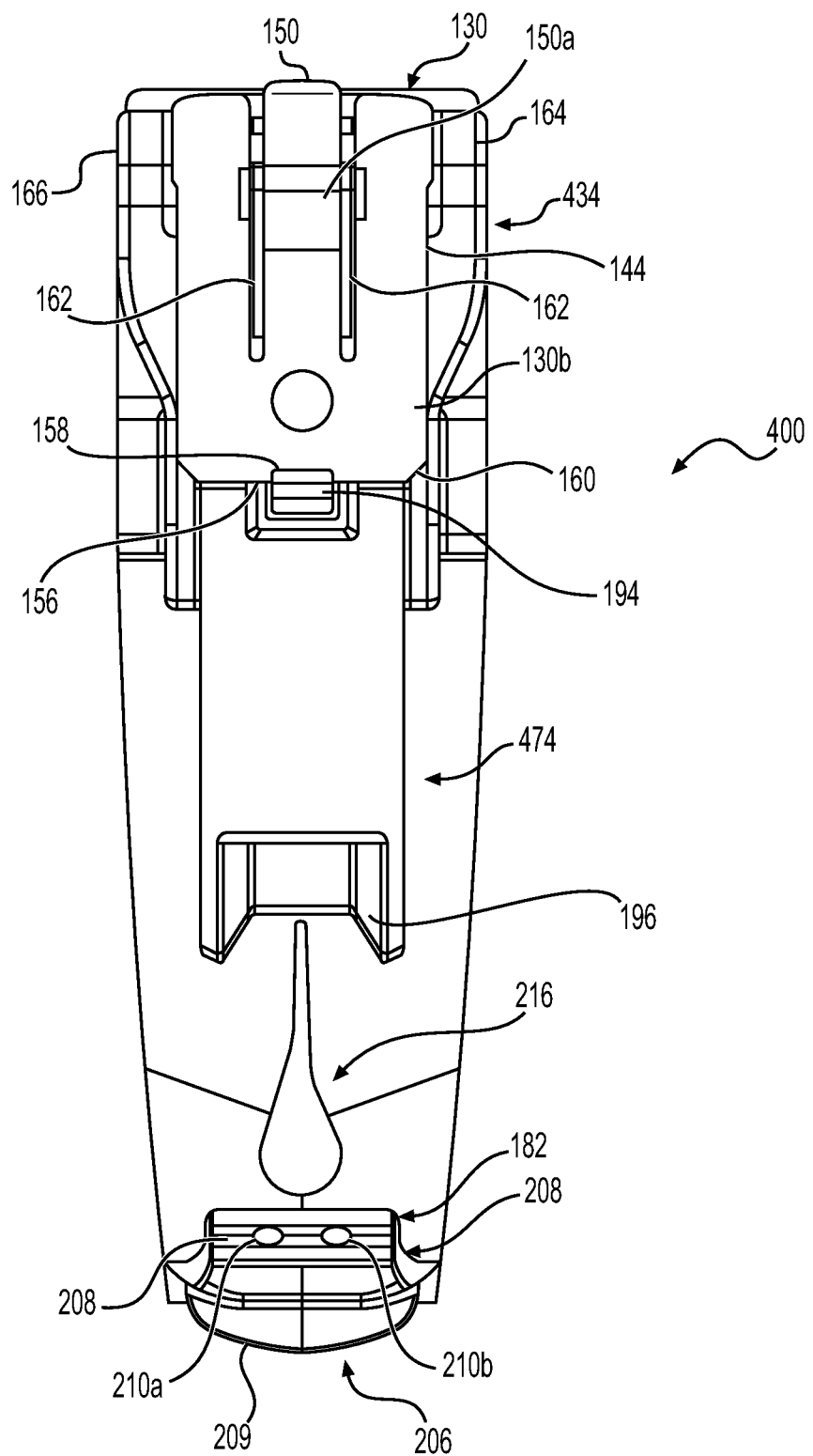
FIG. 11 is a rear view of the pump clip of FIG. 8.

Generally, with reference to FIG. 11, the first lock tab 150 includes a snap fit feature, which engages with the notch 118 (FIG. 8) of the fluid infusion device 102 via a snap-fit engagement in the first, engaged position. The snap fit feature, in one example, is the projection 150a, which extends outwardly from the first lock tab 150 on the second mount side 144. The projection 150a provides the tactile and audible feedback to the user when the pump clip 400 is coupled to the fluid infusion device 102. The first lock tab 150 also includes a graspable portion that provides a contact surface for the user to remove or uncouple the pump clip 400 from the fluid infusion device 102.

With reference to FIG. 9, the hinge pin 132 movably or pivotally couples the base 434 to the mount 130, and defines the first pivot axis. The first pivot axis is substantially perpendicular to a longitudinal axis L3 of the pump clip 400. With reference back to FIG. 10, the first end of the hinge pin 132 is received within a first pivot arm 164 of the base 434 and through the first mount pin post 152; and the second end of the hinge pin 132 is received within a second pivot arm 166 of the base 434 and through the second mount pin post 154.

The base 434 is generally composed of biocompatible polymeric material, including, but not limited to, copolyester (Tritan® TX1001 or Tritan® COPOLYESTER MX711), Polyphenylene Sulfide (Fortron® 1200L1), Nylon (Zytel® ST801AW), Polyoxymethylene (Hostaform® MT12U03, Delrin® 500P, and Delrin® SC655), Polyurethane (Isoplast® 2531 or Isoplast® 2510) and polycarbonate. The base 434 may be formed using casting, printing, molding or another suitable technique. The base 434 includes the first base end 168 opposite a second base end 470, and a first base side 472 (FIG. 4) opposite a second base side 474.

The first base end 168 includes the first pivot arm 164, the second pivot arm 166 and the pivot guide 176. The first pivot arm 164, the second pivot arm 166 and the pivot guide 176 are spaced apart along the first base end 168 so that the first mount pin post 152 and the second mount pin post 154 may be received between the first pivot arm 164, the second pivot arm 166 and the pivot guide 176. In one example, the first mount pin post 152 is positioned between the first pivot arm 164 and an end of the pivot guide 176; and the second mount pin post 154 is positioned between an opposite end of the pivot guide 176 and the second pivot arm 166. The first pivot arm 164 defines a first pivot bore, which receives the first end of the hinge pin 132. The second pivot arm 166 defines a second pivot bore, which receives the second end of the hinge pin 132. The pivot guide 176 defines a concave recess, which further guides the base 434 for rotation about the hinge pin 132. In this example, the concave recess contacts the midsection of the hinge pin 132 for guiding the base 434 in rotation about the hinge pin 132. The pivot guide 176 also defines a sloped surface on the second base side 174. The sloped surface provides clearance for the movement or flexing of the first lock tab 150 during coupling and uncoupling of the pump clip 400 from the fluid infusion device 102.

The first pivot arm 164, the second pivot arm 166 and the pivot guide 176 also cooperate to serve as a stop for limiting a rotation of the clip 140 relative to the base 434. In addition, the first pivot arm 164, the second pivot arm 166 and the pivot guide 176 cooperate with the mount 130 and the first clip end 178 of the clip 140 to define a substantially planar support surface, generally labeled 180 in FIG. 9. With reference to FIG. 9, the support surface 180 is defined along a first end 400a of the pump clip 400. In this example, the first mount end 146 of the mount 130, the first base end 168 of the base 434 and the first clip end 178 of the clip 140 each extend along the axis A, which is transverse to and in this example, perpendicular to the longitudinal axis L3 of the pump clip 400. As will be discussed, the support surface 180 enables the pump clip 400 to be rested a surface, such as a table or the like, to be free standing or to provide a flat surface to apply a force to facilitate the user's use of a first tube clamp 182 or a second tube clamp 184 (FIG. 10), which are incorporated into the clip 140 proximate a second end 400b of the pump clip 400. The support surface 180 increases a user's leverage when using the first tube clamp 182, and the user is able to use both hands to clamp the tube 126 (FIG. 8) with the second tube clamp 184. This provides the user with convenience and ease of use, which increases user satisfaction.

The second base end 470 extends for a second distance beyond the second lock tab 158. Generally, the second base end 470 extends for a distance D3 along the longitudinal axis L3, which is different, and less than the distance D1 that the clip 140 extends. This enables an article of clothing, belt, strap, etc., associated with the user to be received between the clip 140 and the first base side 472 of the base 434. In addition, by extending the distance D3, the second base end 470 maintains clearance to receive the tube 126 (FIG. 8) through the second tube clamp 184 defined through the clip 140. The second base end 470 also defines a clamp projection 476. The clamp projection 476 cooperates with the clip 140 to define a slot 480 for capturing an article of clothing or other item associated with the user to secure the pump clip 400 to the particular article of clothing or other item. In one example, the clamp projection 476 includes a clamp protrusion 476a, which extends outwardly and away from a surface of the clamp projection 476. In this example, the clamp protrusion 476a is substantially triangular, and is shaped to define a surface of contact that engages with the second clip side 202 of the clip 140. The engagement of the clamp protrusion 476a with the second clip side 202 of the clip 140 assists the pump clip 400 in further clamping or gripping onto an article of clothing or item associated with the user, such as a shirt, belt, strap, etc.

Figure 13:
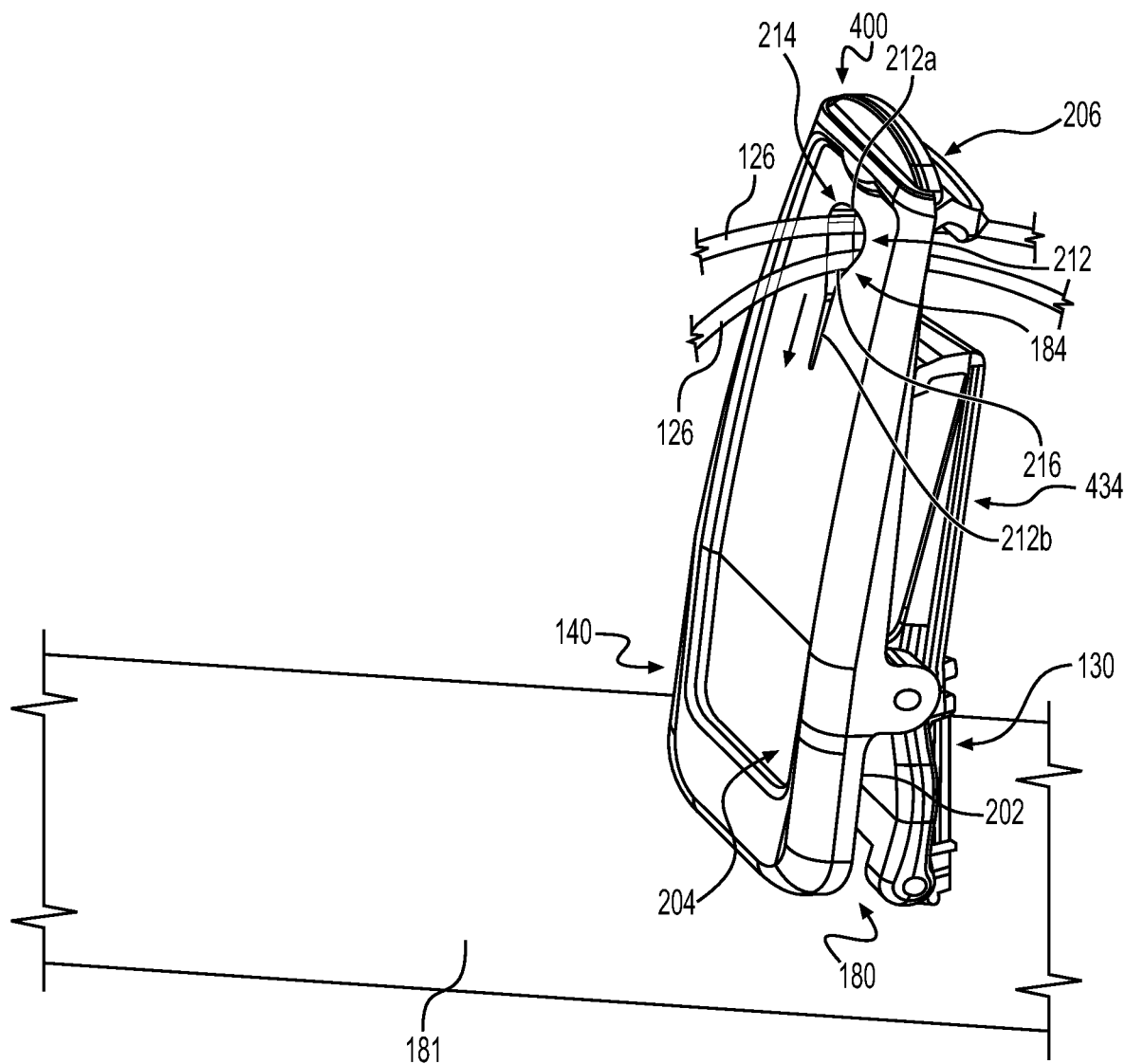
FIG. 13 is a schematic environmental illustration of the pump clip of FIG. 9, in which a first tube clamp is being used to clamp the tube of the infusion set assembly.

In one example, the clamp protrusion 476a includes the at least one or the pair of notches 210a, 210b. As discussed, each of the notches 210a, 210b is sized and shaped to receive a portion of the tube 126 (FIG. 8) associated with the infusion set assembly 104. Thus, in this example, the notches 210a, 210b define semi-circular recesses, which are spaced apart along the clamp protrusion 476a. In order to clamp the tube 126 (FIG. 8) using the clamp projection 476, one of the notches 210a, 210b may be aligned and positioned over the tube 126 (FIG. 13). It should be noted that the spacing of the notches 210a, 210b in FIG. 10 is merely exemplary, as the notches 210a, 210b may have any desired spacing to clamp the tube 126 (FIG. 13). Generally, however, the notches 210a, 210b are spaced apart from opposed sides of the clamp protrusion 476a to provide stability during the clamping of the tube 126 (FIG. 13). Moreover, while two notches 210a, 210b are shown, the clamp protrusion 476a need not include any of the notches 210a, 210b, if desired.

Thus, the clamp projection 476 enables the pump clip 400 to clamp onto an article of clothing or other item associated with the user, enables the pump clip 400 to clamp a portion of the tube 126 (FIG. 8) and the slot 480 also enables the pump clip 400 to be retained about a belt, strap, etc. associated with the user, if desired. Thus, it should be understood that the pump clip 400 is not limited to use just with belts or straps associated with a user. In addition, it should be understood that the clamp projection 476 need not include the clamp protrusion 476a, but rather, the clamp projection 476 may be smooth, if desired. The clamp projection 476 is shown to extend upwardly from the base 434 at an angle or along an axis A4, which is transverse or oblique to the longitudinal axis L3. In other embodiments, the clamp projection 476 may extend along the axis A4, which is perpendicular to the longitudinal axis L3.

With reference to FIG. 10, the first base side 472 includes the first clip pin post 188 and the second clip pin post 190. The first base side 472 may also define a recess 191 near the first base end 168 to receive the spring 138. The spring retainer 192 is defined in the recess 191, and is coupled to the spring 138 to retain the spring 138 on the base 434. In this example, a leaf of the spring 138 engages the recess 191, or pocket, within the base 434. The recess 191, or pocket together with the post or the spring retainer 192, securely holds the leaf of the spring 138.

The first clip pin post 188 and the second clip pin post 190 each extend outwardly and away from the first base side 472. The first clip pin post 188 and the second clip pin post 190 are spaced apart from each other the first base side 472 such that the first clip pin post 188 and the second clip pin post 190 are on opposed sidewalls of the base 434. Generally, the first clip pin post 188 and the second clip pin post 190 are spaced apart to enable the spring 138 to be received between the first clip pin post 188 and the second clip pin post 190. The first clip pin post 188 defines a first clip bore, and the second clip pin post 190 defines a second clip bore. The first clip bore and the second clip bore are coaxially aligned along an axis to receive the clamp pin 136 therethrough to pivotally couple the clip 140 to the base 434. Thus, the hinge pin 132 is used to connect the mount 130 to the base 434 which allows for pivotal movement of the mount 130 relative to the base 434. The hinge pin 132 is inserted through the pair of mount pin bores of the first mount pin post 152 and the second mount pin post 154 of the opposed sidewalls of the mount 130 and the first pivot arm 164 and the second pivot arm 166 of the opposed sidewalls of the base 434. The first base side 472 faces the second clip side 202 to define the slot 480.

With reference to FIG. 11, the second base side 474 defines the second lock tab 158, the slot 194 and the recess 196. The second lock tab 158 cooperates with the lip 156. In this regard, in the lock position, the lip 156 is received on or rests on the second lock tab 158. In the unlock position, the lip 156 no longer contacts or is released from the engagement with the second lock tab 158 (FIG. 10). Generally, a thickness of the second lock tab 158 provides an interference onto which the lip 156 is received. The slot 194 enables the second lock tab 158 to move or flex to release the lip 156. The slot 194 may be defined between the second lock tab 158 and the first base end 168. The recess 196 may defined through a portion of the second base side 174 near or adjacent to the second lock tab 158, and may be defined near or adjacent to the second lock tab 158 to the second base end 170. The recess 196 provides a mass savings.

With reference to FIG. 9, the clamp pin 136 movably or pivotally couples the clip 140 to the base 434, and defines a second pivot axis. The second pivot axis is substantially perpendicular to the longitudinal axis L3 of the pump clip 400, and is substantially parallel to the first pivot axis defined by the hinge pin 132. Generally, the second pivot axis is offset from or spaced apart from the first pivot axis defined by the hinge pin 132 along the longitudinal axis L3 of the pump clip 400. With reference to FIG. 10, the first end of the clamp pin 136 is received through the first clip pin post 188; and the second end of the clamp pin 136 is received through the second clip pin post 190. The clamp pin 136 is received within the clip coupling posts 198, 199 of the clip 140.

The spring 138 is coupled to the base 434. The spring 138 is compressible by a force applied to the clip 140 to move the clip 140 from a first, clamped position to a second, release position. In one example, the force needed to overcome the spring 138 to move the clip 140 from the first, clamped position (fully closed position) is about 1 pound-force (lbf.), and the force needed to move the clip 140 to the second, release position (fully opened position) is about 6 pound-force (lbf.). The spring 138 defines a spring bore in one of the leaves for coupling the spring 138 to the spring retainer 192 of the base 434.

As discussed, with reference to FIG. 9, the clip 140 cooperates with the base 434 to define the slot 480 for receipt of an article of clothing or item associated with the user, such as a shirt, belt, strap, etc. between the second clip side 202 of the clip 140 and the base 434 when the clip 140 is in the first, clamped position. The clip 140 includes the first clip side 204 opposite the second clip side 202, the first clip end 178 opposite the second clip end 206, the first tube clamp 182 and the second tube clamp 184.

With reference to FIG. 10, the first clip side 204 is substantially smooth, and includes a recessed surface 207 that extends from proximate the first clip end 178 to the second clip end 206. The second clip side 202 is substantially smooth, and includes the pair of clip coupling posts 198, 199, which extend outwardly from the second clip side 202 near the first clip end 178. The clip coupling posts 198, 199 each receive the clamp pin 136. Thus, the clip 140 is rotatably mounted to the base 434 by the clamp pin 136 inserted through the clip coupling posts 198, 199 of the clip 140 and the pair of the clip bores of the first clip pin post 188 and the second clip pin post 190, respectively, on the opposed sidewalls of the base 434.

The second clip side 202 also includes the hook or clip projection 208 at the second clip end 206. The clip projection 208 extends outwardly from the second clip side 202, and forms a substantially U-shape with the second clip side 202. The clip projection 208 cooperates with the base 434 (FIG. 8) to define a tortuous path for capturing an article of clothing or other item associated with the user to secure the pump clip 400 to the particular article of clothing or other item. In one example, the clip projection 208 includes the protrusion 208a, which extends outwardly and away from a surface of the clip projection 208. The clip projection 208 enables the clip 140 to clamp onto an article of clothing or other item associated with the user, and the slot 480 defined between the second clip side 202 and the base 434 also enables the pump clip 400 to be retained about a belt, strap, etc. associated with the user, if desired.

The second clip side 202 also has the recess which engages the spring 138. The spring 138 is in compression in the assembly when the clip 140 is in the first, clamped position such that in the first, clamped position shown in FIG. 9, the clip projection 208 at the second clip end 206 of the clip 140 is in compression resting on the fluid infusion device 102 and/or the article associated with the user, which provides better attachment of the pump clip 400 on the article associated with the user, such as a shirt, belt, strap, etc. When a force F applied to the first clip end 178 of the clip 140 exceeds the spring force from spring 138, the clip 140 rotates about the second pivot axis defined by the clamp pin 136 and the second clip end 206 of the clip 140 is moved to the second, release position in which the clip 140 is open relative to the fluid infusion device 102 (FIG. 8) and the base 434.

With reference to FIG. 11, the first tube clamp 182 is defined on the protrusion 208a of the clip projection 208. In this example, the first tube clamp 182 comprises the pair of notches 210a, 210b. The second tube clamp 184 is defined through the clip 140 from the first clip side 204 to the second clip side 202 proximate the second clip end 206. The second tube clamp 184 comprises the generally tear-drop shaped opening 212. The opener tab 209 extends outwardly at the second clip end 206. The opener tab 209 is generally arcuate or curved, and is shaped to fit within a battery cap (not shown) associated with the fluid infusion device 102. In certain instances, the user may also employ the pump clip 400 to unlock a battery cap associated with the fluid infusion device 102 to replace a battery, for example. It should be noted that while the opener tab 209 is described herein as being used to open a battery cap associated with the fluid infusion device 102, generally, the opener tab 209 may be used as a flat head screwdriver, and thus, may be used to open or unscrew various other items.

In one example, with reference to FIG. 10, in order to assemble the pump clip 400, with each of the mount 130, the hinge pin 132, the base 434, the spring 138, the clamp pin 136 and the clip 140 formed, the base 434 may be coupled to the mount 130 such that the lip 156 of the mount 130 engages the second lock tab 158 of the base 434. With the first pivot arm 164 and the second pivot arm 166 of the base 434 coaxially aligned with the first mount pin post 152 and the second mount pin post 154, the hinge pin 132 may be inserted through the first pivot arm 164 and through to the second pivot arm 166 to couple the base 434 to the mount 130. The spring 138 may be positioned within the recess defined on the first base side 172, and the spring bore of the spring 138 may be coupled to the spring retainer 192 to couple the spring 138 to the base 434. The clip 140 may be positioned over the base 434 such that the clip coupling posts 198, 199, the first clip pin post 188 and the second clip pin post 190 are coaxially aligned. The clamp pin 136 is inserted through the clip coupling posts 198, 199, the first clip pin post 188 and the second clip pin post 190 to couple the clip 140 to the base 434.

With the pump clip 400 assembled, the pump clip 400 may be coupled to the fluid infusion device 102. In one example, with reference to FIG. 8, with the pump clip plate 112 defined on the fluid infusion device 102, the arms 130a, 130b on the mount 130 are aligned with the slots 114a, 116a of the rails 114, 116 on the fluid infusion device 102. The arms 130a, 130b on the mount 130 are inserted into the rails 114, 116, such that the arms 130a, 130b slide along the slots 114a, 116a until the projection 150a of the first lock tab 150 engages the notch 118 on the fluid infusion device 102. Once the first lock tab 150 engages, a tactile and audible feedback is provided to the user to indicate the pump clip 400 is fully installed.

With the pump clip 400 fully installed on the fluid infusion device 102, the pump clip 400 and the fluid infusion device 102 may be coupled to user, by positioning an article of the user's clothing, for example, between the clamp projection 476 and the second clip side 202. When coupled to the user, the mount 130 is movable relative to the base 434 to compensate for forces applied to the fluid infusion device 102. In one example, if the fluid infusion device 402 encounters a force, due to the fluid infusion device 102 encountering a seat belt, arm of a chair, door knob, a force applied by a user, etc., the lip 156 resists the force until the force overcomes the lip 156 and the lip 156 disengages with the base 434. Once the lip 156 disengages from the base 434, the mount 130 moves or pivots from the first position, toward the second position or to a position between the first position and the second position. In the second position, the mount 130 is rotated about the hinge pin 132 away from the base 434, which enables the pump clip 400 to absorb the force, without breaking the pump clip 400 and/or damaging the fluid infusion device 102. By absorbing this force, the pump clip 400 also ensures that the infusion set assembly 104 remains coupled to the user. Alternatively, the user may be the source of the force, as the movement of the mount 130 relative to the base 434 enables the user to rotate the fluid infusion device 102 to view a screen of the fluid infusion device 102 without requiring a removal of the pump clip 400 from the user.

In addition, with reference to FIG. 9, the clip 140 is movable or pivotable about the second pivot axis defined by the clamp pin 136 based on an application of the force F to the first clip end 178 of the clip 140, which in one example, may range from about 10 degrees to about 45 degrees. It should be understood that the clip 140 may pivot to various other positions between the maximum of about 45 degrees and the first position (FIG. 9), depending upon an amount of the force F applied by the user.

In order to remove or uncouple the pump clip 400 from the fluid infusion device 102, in one example, a force is applied by the user, which lifts up the first lock tab 150. With the first lock tab 150 lifted up, a force is applied by the user to a rear surface of the first lock tab 150 to disengage the lip 156 with the second lock tab 158 of the base 434. Once the lip 156 is disengaged, the pump clip 400 may be moved to slide the arms 130a, 130b toward the notch 118. Once the arms 130a, 130b are removed or disengaged with the slots 114a, 116a of the rails 114, 116, the pump clip 400 is uncoupled or removed from the fluid infusion device 102.

Figure 12:
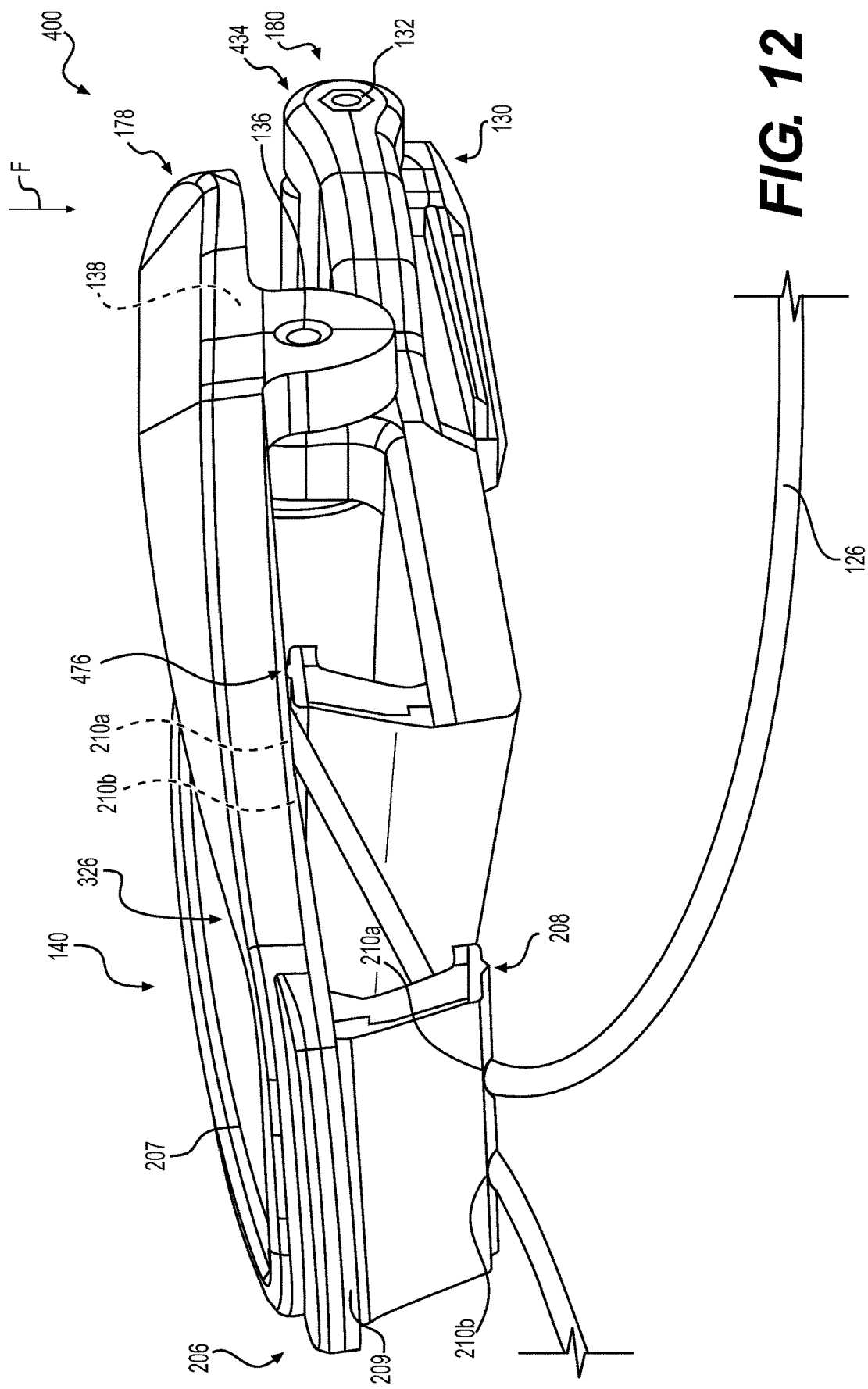
FIG. 12 is a schematic environmental illustration of the pump clip of FIG. 9, in which a second tube clamp is being used to clamp the tube of the infusion set assembly.

With the pump clip 400 removed from the fluid infusion device 102, the pump clip 400 may be used to perform one or more tests of the fluid infusion device 102. In certain instances, the user may be directed to occlude or inhibit the flow of the fluid through the infusion set assembly 104 (FIG. 8) to diagnose or test certain functions of the fluid infusion device 102. In order to use the first tube clamp 182, when directed, with reference to FIG. 12, one of the notches 210a, 210b may be positioned over the portion of the tube 126. The user may place their hand on the support surface 180, and may apply a force to the pump clip 400 to use the respective one of the notches 210a, 210b to inhibit the flow of the fluid through the tube 126 or to clamp the tube 126 (FIG. 8) with the first tube clamp 182. Optionally, the user may apply a force to the first clip end 178 to move the clip 140 relative to the base 434 such that the portion of the tube 126 is received within the notches 210a, 210b of the clamp protrusion 476a. The user may release the force from the first clip end 178, and the portion of the tube 126 may be clamped between the second clip side 202 and the notches 210a, 210b of the clamp protrusion 476a.

Alternatively, with the pump clip 400 removed from the fluid infusion device 102, in order to use the first tube clamp 182 to occlude or inhibit the flow of the fluid through the tube 126 of the infusion set assembly 104 (FIG. 8), when directed, with reference to FIG. 13, the user may insert the tube 126 through the bulbous opening portion 214. The user may position the support surface 180 of the pump clip 100 on the surface 181, such as a table, and may push the portion of the tube 126 from the bulbous opening portion 214 at the first end 212a toward the slit 216. As the tube 126 advances within the opening 212, the portion of the tube 126 is compressed. Once the tube 126 is positioned within the slit 216 at the second end 212b, the flow of the fluid through the tube 126 (FIG. 8) is inhibited such that the tube 126 is clamped by the second tube clamp 184.

By providing the first tube clamp 182 and the second tube clamp 184 integrally formed or monolithic with the clip 140 or the first tube clamp 182 integrally formed with or monolithic with the clip 306, the user has the first tube clamp 182 and/or the second tube clamp 184 with them when a test of the fluid infusion device 102 is needed. Moreover, by providing the first tube clamp 182 and/or the second tube clamp 184 integrally formed or monolithic with the clip 140, 306, the user may use the pump clip 100, 300, 400 as leverage to clamp the tube 126 (FIG. 1), without requiring additional tools. Further, by providing the pump clip 100, 300, 400 with the support surface 180, the user may use the first tube clamp 182 and/or the second tube clamp 184 with a single hand or with both hands, if desired. In addition, by integrally forming the opener tab 209 with the pump clip 100, 300, 400, the pump clip 100, 300, 400 may also be used by the user to remove the battery cap of the fluid infusion device 102, which provides the user with convenience.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A pump clip for a fluid infusion device system, comprising:
   a mount to be connectable to a fluid infusion device;
   a base coupled to the mount, the base pivotable relative to the mount about a first pivot axis; and
   a clip coupled to the base, the clip pivotable relative to the base about a second pivot axis, the clip defines at least one tube clamp to receive a tube associated with the fluid infusion device, and the at least one tube clamp comprises at least one notch defined in a clip projection that extends outwardly near a second end of the clip.

2. The pump clip of claim 1, wherein the base extends for a distance along a longitudinal axis of the pump clip, the clip extends for a second distance along the longitudinal axis and the distance is less than the second distance.

3. The pump clip of claim 2, wherein the base has a clamp protrusion that extends outwardly from the base and is configured to contact the clip to define a slot.

4. The pump clip of claim 1, wherein the clip defines two tube clamps.

5. The pump clip of claim 1, wherein the at least one notch comprises two notches, which are defined in a protrusion that extends outwardly from a surface of the clip projection and the two notches are spaced apart along the protrusion.

6. The pump clip of claim 1, wherein the clip has a first end opposite the second end, and the clip is coupled to the base proximate the first end.

7. A pump clip for a fluid infusion device system, comprising:
   a mount to be connectable to a fluid infusion device;
   a base coupled to the mount, the base pivotable relative to the mount about a first pivot axis; and
   a clip coupled to the base, the clip pivotable relative to the base about a second pivot axis, the clip defines at least one tube clamp to receive a tube associated with the fluid infusion device, the at least one tube clamp comprises at least one opening defined through a first side of the clip and the at least one opening includes a bulbous portion and a slit, with the bulbous portion defined at a first end of the at least one opening to receive the tube and the slit defined in a second end of the at least one opening to clamp the tube.

8. The pump clip of claim 7, wherein the bulbous portion includes a pair of sloped sides that transition to the slit.

9. The pump clip of claim 7, wherein the at least one opening is asymmetric relative to a longitudinal axis of the pump clip.

10. The pump clip of claim 7, wherein a first mount end of the mount, a first base end of the base and a first clip end of the clip extend along an axis and cooperate to define a support surface at a first end of the pump clip.

11. The pump clip of claim 10, wherein the at least one tube clamp is defined proximate a second end of the pump clip, the second end opposite the first end.

12. A fluid infusion device system, comprising:
    a fluid infusion device having a pump clip interface;
    a pump clip coupled to the pump clip interface, the pump clip including:
      a mount configured to be slidably received within the pump clip interface, the mount having a first mount end;
      a base coupled to the mount at the first mount end, the base pivotable relative to the mount about a first pivot axis and the base having a first base end; and
      a clip coupled to the base, the clip pivotable relative to the base about a second pivot axis, the clip having a first clip end opposite a second clip end, the clip defines at least one tube clamp proximate the second clip end to receive a tube associated with the fluid infusion device, and the first mount end, the first base end and the first clip end extend along an axis, which is transverse to a longitudinal axis of the pump clip to define a support surface for the pump clip.

13. The fluid infusion device system of claim 12, wherein the base extends for a distance along the longitudinal axis of the pump clip, and the clip extends for a second distance along the longitudinal axis, with the distance less than the second distance.

14. The fluid infusion device system of claim 12, wherein the clip further comprises an opener tab configured to unlock a battery cap associated with the fluid infusion device.

15. The fluid infusion device system of claim 12, wherein the at least one tube clamp comprises at least one notch defined in a clip projection that extends outwardly near a second end of the clip.

16. The fluid infusion device system of claim 12, wherein the at least one tube clamp comprises at least one opening defined through a first side of the clip that is asymmetric relative to the longitudinal axis of the pump clip.

17. A fluid infusion device system, comprising:
    a fluid infusion device having a pump clip interface;
    a pump clip coupled to the pump clip interface, the pump clip including:
      a mount configured to be slidably received within the pump clip interface, the mount having a first mount end;
      a base coupled to the mount at the first mount end, the base pivotable relative to the mount about a first pivot axis, the base extending for a distance along a longitudinal axis of the pump clip and the base having a first base end; and
      a clip coupled to the base, the clip pivotable relative to the base about a second pivot axis, the clip having a first clip end opposite a second clip end, the clip extending for a second distance along the longitudinal axis, which is greater than the distance of the base, the clip defines at least one tube clamp proximate the second clip end to receive a tube associated with the fluid infusion device, and the first mount end, the first base end and the first clip end extend along an axis, which is transverse to the longitudinal axis of the pump clip to define a support surface for the pump clip.

18. The fluid infusion device system of claim 17, wherein the clip further comprises an opener tab configured to unlock a battery cap associated with the fluid infusion device.

* * * * *